US012805982B2

(12) United States Patent
Martz et al.

(10) Patent No.: US 12,805,982 B2
(45) Date of Patent: Nov. 24, 2026

(54) MANUFACTURE OF ORTHODONTIC APPLIANCES

(71) Applicant: ArchForm, Inc., Santa Clara, CA (US)

(72) Inventors: Martin Martz, Sunnyvale, CA (US); Andrew Martz, Sunnyvale, CA (US)

(73) Assignee: ArchForm, Inc., Santa Clara, CA (US)

(*) Notice: Subject to any disclaimer, the term of this patent is extended or adjusted under 35 U.S.C. 154(b) by 119 days.

(21) Appl. No.: 18/621,777

(22) Filed: Mar. 29, 2024

(65) Prior Publication Data

US 2024/0325119 A1 Oct. 3, 2024

Related U.S. Application Data

(60) Provisional application No. 63/455,306, filed on Mar. 29, 2023.

(51) Int. Cl.

*A61C 7/28* (2006.01)
*A61C 7/00* (2006.01)
*G16H 50/50* (2018.01)

(52) U.S. Cl.

CPC .............. *A61C 7/282* (2013.01); *A61C 7/002* (2013.01); *G16H 50/50* (2018.01)

(58) Field of Classification Search

CPC ......... A61C 7/282; A61C 7/002; G16H 50/50
See application file for complete search history.

(56) References Cited

U.S. PATENT DOCUMENTS

| | | | | |
|---|---|---|---|---|
| 7,063,532 | B1 * | 6/2006 | Jones | A61C 7/00 433/213 |
| 2008/0026338 | A1 * | 1/2008 | Cinader | A61C 1/084 433/29 |
| 2013/0317800 | A1 * | 11/2013 | Wu | G06T 19/20 703/11 |
| 2015/0359614 | A1 * | 12/2015 | Sachdeva | A61C 7/002 433/29 |
| 2017/0273760 | A1 * | 9/2017 | Morton | A61C 7/002 |
| 2018/0098829 | A1 * | 4/2018 | Fisker | A61C 13/01 |
| 2019/0388189 | A1 * | 12/2019 | Shivapuja | A61C 7/002 |

* cited by examiner

*Primary Examiner* — Terrell M Robinson

(74) *Attorney, Agent, or Firm* — Cognition IP, P.C.; Edward Steakley

(57) ABSTRACT

A system may display a user interface depicting a model of a patient's teeth and the patient's palate and/or the buccal shelf area. The palate and/or the buccal shelf area depict one or more implants. The system determines a non-moveable zone about the model via receiving a user input identifying the one or more non-moveable zones. The system generates multiple electronic versions of aligners configured to fit over the one or more implants and the patient's teeth. Wearing of successive aligners cause the patient's teeth to move in a direction toward a correction, while the aligners have non-moveable zones that remain in a fixed location in relationship to the one or more implants.

18 Claims, 19 Drawing Sheets

800

MANUFACTURE OF ORTHODONTIC APPLIANCES

CROSS-REFERENCE TO RELATED APPLICATIONS

This application claims the benefit of priority to U.S. Provisional Application No. 63/455,306, filed on Mar. 29, 2023, which is hereby incorporated by reference in its entirety.

BACKGROUND

Dental aligners, specifically dental aligners may be formed in a series of discrete small steps through the method of digital computer software manipulation of 3-D tooth images. A dentist or orthodontist starts with a 3-dimensional intra-oral digital scan of a patient's teeth which produces a 3-D digital surface scan representing the positions of teeth in their natural, unstraightened state. Alternatively, dental impressions could be obtained of the patient's teeth, and dental plaster or dental stone could be poured into the dental impressions to produce a set of upper and lower casts representing the teeth. A digital scanner could then be used to produce a 3-D digital surface scan of the models of the teeth.

SUMMARY

In general terms, this disclosure is directed to a dental appliance to cause orthodontic intrusion of posterior teeth. For example, the dental appliance may improve bite closure by causing the orthodontic intrusion of both upper and lower posterior teeth. The dental appliances provide alignment of teeth relative to one or more temporary attachment devices. Moreover, the disclosure is directed to software applications for the design and manufacture of dental appliances. The TADS provide a fixed point of reference with regard to the design of a series of dental appliances used for the correction to primarily to cause anterior or posterior changes to the teeth.

The details of one or more aspects are set forth in the accompanying drawings and description below. Other features and advantages will be apparent from a reading of the following detailed description and a review of the associated drawings. It is to be understood that the following detailed description is explanatory only and is not restrictive of this disclosure.

DETAILED DESCRIPTION

Figure 1A:
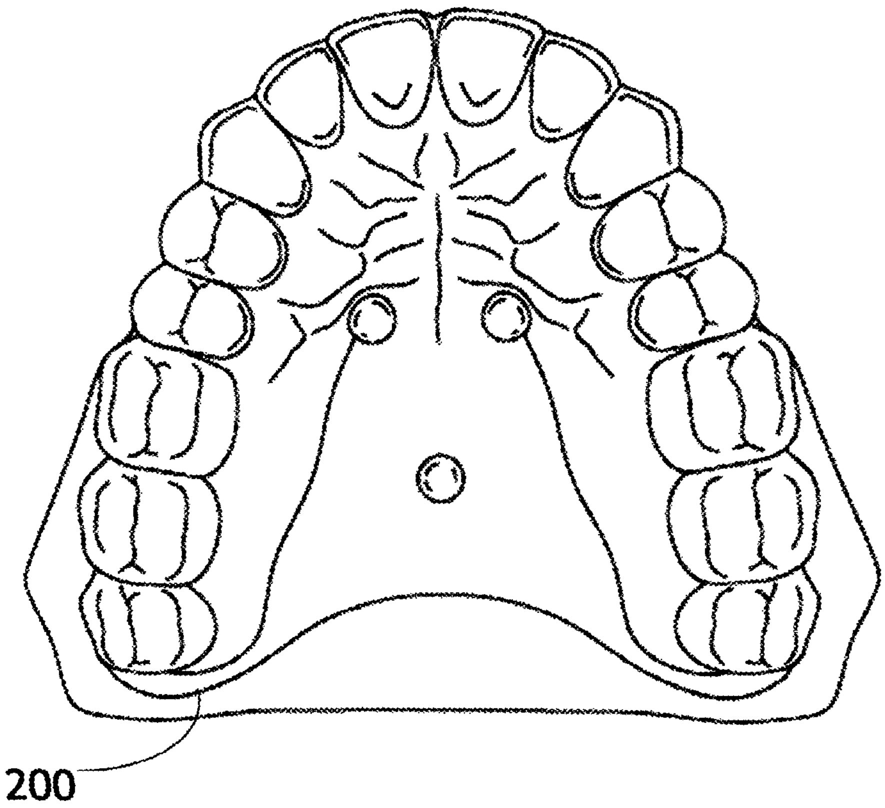
FIG. 1A is a diagram of an example of an aligner placed over the teeth and palate and affixed to temporary anchorage devices.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the technology disclosed herein.

The present disclosure relates to fabrication of dental appliances that are usable to provide therapy to a patient. In particular, the present disclosure relates to fabrication of orthodontic appliances such as orthodontic aligners.

The technology disclosed herein can be used to generate an orthodontic aligner for a patient to apply an intrusive force to the patient's teeth. In some implementations, the orthodontic aligner may be part of a series of removable orthodontic aligners to reposition a patient's teeth over time. The technology can be used to fabricate the appliance fully or partially within an office of a medical professional.

In some implementations, orthodontic positioners (or aligners) are made from a set of plaster models derived from three-dimensional (3D) negative dental impressions of a patient's teeth. The plaster dental models are then modified by cutting the teeth apart using a small jeweler's saw or rotary cutting discs, followed by repositioning the plaster teeth in a better, straighter, desired arrangement, and then holding the teeth in the new arrangement with dental wax.

The repositioned teeth molds provide the basis for manufacturing the positioners. The resilience of the material from which the positioner is made provides the energy to move the teeth from their original position toward the new straightened position. A series of aligners may be made to move the teeth in incremental steps. Making a series of appliances is difficult, time-consuming, and error-prone when the tooth arrangement for each step must be made by hand using plaster and wax.

Digital technologies can be used to overcome at least some of the difficulties associated with fabricating a series of aligners that move teeth incrementally. Computer Aided- Design (CAD)/Computer-Aided Manufacturing (CAM) software can be used to produce tooth models, from which a progressive series of appliances can be manufactured. The tooth models can be generated from 3D images of the patient's dentition. These tooth models can then be repositioned and used to form aligners. For example, the repositioned tooth models can be used to fabricate dental models upon which aligners are formed using a combination of vacuum, pressure, and heat. This forming process is informally referred to within the orthodontic laboratory community as the "suck down" process.

In one process for producing a series of aligners, a technician first scans a patient's dental model to obtain CAD-manipulatable virtual models of a patient's dental anatomy. A dental model normally consists of one upper and one lower plaster model of the teeth, palate, and gums. Once the virtual model of the original malocclusion has been obtained, a technician will then undertake steps involving extensive manipulation of the virtual malocclusion. This involves extensive repositioning of the teeth according to a comprehensive and sequential procedure, ultimately arriving at a finished or ideal occlusion for that patient. The finished occlusion in the virtual model is consistent with the complete repositioning of the patient's upper and lower occlusion that would result at the end of successful conventional orthodontic treatment. After the steps described above are accomplished, the technician possesses two versions of the patient's teeth available within the virtual CAD environment. One version represents the original malocclusion and the other represents the ideal occlusion. In other words, the technician has models representing the beginning and end states of the patient's teeth.

Another step in the process involves the creation of an incremental, progressive series of physical forming models. Each of these forming models represents a snapshot of the patient's future occlusion at specific incremental steps along the patient's proposed treatment sequence between the beginning and the end conditions as described above. To accomplish this, the technician creates a virtual first transition model. This virtual first transition model represents some or all of the teeth being subtly moved from their original pre-treatment positions to a virtual first transition position that is in the direction of their intended finished positions. Additional virtual transition models can be created similarly. In this manner, the technician creates a series of progressive models, with each biased slightly further than the previous one, and each moves the teeth slightly closer to their finished target positions. A final forming model will take the teeth from the series of transition positions and move them into their final, desired positions.

Once such a series of virtual intermediate forming models has been created and a final forming model has been created by the technician, digital code representing each of the models in the series is directed to operate a rapid prototyping machine. Within a rapid prototyping machine, series of physical forming models are produced using any of a number of conventional processes, such as computer numerically-controlled (CNC) machining, stereo lithography, or 3D printing. The production step results in the production of hard, physical models that correspond to each of the series of virtual intermediate models and the final model.

In another step of the process, each of the series of physical models is mounted in a vacuum machine (also referred to as a suck-down machine) where a combination of pressure, heat, and vacuum is used to form the actual series of progressive aligners from plastic sheet material of a constant thickness. Once the series of progressive aligners are formed and trimmed, they are sequentially labeled, packaged, and shipped to the attending orthodontist. The orthodontist then schedules an appointment for the patient, at which time the aligners and instructions for their use are given to the patient. The patient is instructed to wear the first set of aligners for a period of time, typically two weeks. After that, the first set is discarded and the patient transitions to the next set of the series and so on.

The aligners can be configured to urge the patient's teeth to move according to the positional biases created virtually by the technician. The teeth are progressively biased and urged to move in desired directions toward their predetermined finished positions by the resilience of the polymeric material of the aligner. Ideally, gentle but continuous forces would be delivered by the aligners, causing certain physiological processes involving the creation and/or restoration of the bone supporting the roots of the teeth to take place. The net result should be the slow, progressive orthodontic movement of the roots of the teeth through the underlying bone toward desirable positions and orientations.

Embodiments of the appliance described herein include a single aligner or one or more aligner from a series of aligners. Some embodiments do not include an aligner, but instead include one or more bands, bars, or brackets that are coupled to the patient's dentition.

Digital scanners, whether of the intra-oral type, or model scanners usually produce two separate scans, one for the upper dental arch, and one for the lower dental arch, as well as digital information indicating accurately how the scans relate to one another in 3-D space, sometimes referred to as the "bite registration." This bite registration typically records the tooth relationship in what is called the "MI" or maximum intercuspal contact relationship. This is usually not the same position as the "CR" position when the Temporo-mandibular joints are fully seated in their maximum "superior-anterior position" in the temporal fossae. The difference between these two positions and whether or not it is important to register this difference has been the subject of debate in the field of dentistry for decades. It is probably sufficient to say, we will not settle the debate here. Currently most orthodontists are willing to accept the maximum intercuspation position delivered by the intra-oral scanners if they have determined clinically that there is not a huge discrepancy between the "MI" position and the "CR" or centric relation position.

Dental software is then used to segment the single-piece scan of the upper dental arch into the separate, discreet teeth and the gum tissue. The software also segments the scan of the lower teeth, as well as relating the positions of the upper teeth to the lower teeth.

To produce a digital incremental orthodontic treatment plan, the software starts with the initial position of the teeth and a software operator moves the teeth to a new, desired position, often achieving certain goals not only in alignment of the teeth but also an improvement in the way the upper and lower teeth fit together, or occlude. The software operator decides, based on certain pre-determined "preferences" that he is allowed to set within the software, how many intermediate stages will be required to achieve his goals, based on the amount of movement he chooses to make. The path each tooth will follow through each of the intermediate stages can be linear or non-linear, and the rate of movement can be determined by the operator. For each of the intermediate stages or steps of movement, a 3-D model can be produced through various means including the use of a 3-D printer, a digitally controlled milling machine, or some other method. Typically, a separating medium is applied over the model, and then a thin sheet of plastic is thermoformed over the model, and the edges are trimmed either manually by hand using scissors or other cutting instruments, or by a 3-D milling machine, or even by a 3-D laser cutter, or other suitable means. Alternatively, the computer can be connected directly to a 3-D printer, and the dental aligner can be printed directly out of clear, or tooth-colored, resilient resin, without the need for a model or thermoformer. This method allows for the aligner to have regions of varying thickness and strength, unlike the thermoformed aligners which are made of a plastic with uniform thickness prior to the thermoforming process.

This filing shares in common the novel features described in the earlier filings including the palatal Temporary Anchorage Device (TAD) with the spherical head, and also the lower arch Temporary Anchorage Device, typically placed on the facial side of the lower second or third molar area sometimes referred to as the "buccal shelf." Another name by which a TAD is commonly called is a "mini-implant." The TAD devices with the spherical heads are designed to directly, but removably engage a portion of the aligners, as will be described further. The aligner material will be shaped to form around the head of the TAD, which if spherical in shape will have a uniform undercut even if the TAD's are not placed with uniformly parallel orientation. If TAD's with head shapes other than spheres are used, such as flattened spheres, or oval nail-head shapes, football shapes, etc., there will still be undercuts that can be used for retention purposes, and these would still fall within the scope of the patent. The aligner material will be shaped to form around the head of the TAD, which if spherical in shape will have a uniform undercut even if the TAD's are not placed with uniformly parallel orientation. If TAD's with head shapes other than spheres are used, such as flattened spheres, or oval nail-head shapes, football shapes, etc, there will still be undercuts that can be used for retention purposes, and these would still fall within the scope of the patent.

In the priority applications, various means to increase the flexibility of the aligner were shown, including flexible arms on the palatal side, and arch-shaped connecting loops on the facial side were used to connect segments of the aligners.

Basic, one-piece aligners have a certain measure of flexibility without these added features. Especially, aligners that are 3-D printed offer the opportunity for increased flexibility in certain areas and increased strength in other areas because the thickness of the material can be varied by the software controlled by the operator. Zones can be outlined and selected to have a certain printed thickness, and these zones can be chosen by the operator uniquely for each case. However, even thermoformed aligners offer a certain innate flexibility. The amount of tooth movement planned for each stage of the aligner can be adjusted for the particular aligner design. The amount of tooth movement planned for each stage of the aligner can be adjusted for the particular aligner design.

In this disclosure, seven basic variations are discussed:

Variation #1

Conventional aligners (whether thermoformed or printed) with partial or complete palatal coverage will directly engage palatally placed TAD's (Temporary Anchorage Devices, sometimes called mini-implants). Most of the palatal TAD's described in this disclosure will be placed in the T-zone as described by Becker, K, Unland, J, Wilmes, B, Taraf, N, Drescher, D in the article "Is there an ideal insertion angle and position for orthodontic mini-implants in the anterior palate? A CBCT study in humans." Published in American Journal of Orthodontics and Dentofacial Orthopedics, 156.3 (2019) 345-354. Most of these, except as described otherwise, will include specially designed spherical head shapes. Lower conventional aligners with an extra facial surface flange extension will directly engage these same special TAD's placed on the buccal bone shelf of the mandible. The software will treat the TAD's just like it treats immovable teeth. They will be identified and segmented away from the surrounding gum tissue surfaces but will not be movable. Their location will be fixed just like an ankylosed tooth, a bridge, or a crown placed over an implant. The TAD supported portions of the aligners will be used in the software to apply force to teeth in other portions of the aligner that the orthodontist wants to move as part of the treatment plan.

Variation #2

Conventional aligners (whether thermoformed or printed) with partial or complete palatal coverage will directly engage palatally placed TAD's or lower buccal bone shelf TAD's in the mandible (as in Variation #1), but in this variation the software provides for cutting planes to define regions around the TAD's (and including the TAD's) that are immovable, both in the palatal region and in the mandible. The immovable regions of the aligner will be used to apply force to move teeth as part of the treatment plan as in Variation #1.

Variation #3

Conventional aligners (whether thermoformed or printed) with partial or complete palatal coverage will directly engage palatally placed TAD's or lower buccal bone shelf TADS's in the mandible (as in Variations #1, 2), but in this variation, there will be a zone selected by the operator of the software, using appropriate selection tools, surrounding either a single TAD or multiple TAD's, but also including the TAD or TAD's, that will be considered by the software to be immovable or fixed in its original location. Alternatively, this zone, including the TAD or TAD's, can be moved by the software separately from the fixed base of the model. The goal is the same as in variations #1, 2, for the software to assist the orthodontist to design a treatment plan using aligners to apply forces to move the teeth to a desired new location, using the TAD's and the surrounding region as anchorage.

Variation #4

One-piece aligners with hooks (of various types) will engage (using elastic bands) with a metallic TAD-retained anchorage structure in the palate as designed by Benedict Wilmes and others and one-piece lower aligners with hooks (of various types) will engage (using elastic bands) directly with TAD's placed on the mandibular buccal shelf. The position of the hooks on both the metallic anchorage structure and on the one-piece aligners can be arranged in various locations relative to both the long axes of certain teeth or to the center of resistance to certain teeth for the most efficient mechanical advantage for the desired movements. These are aligners designed specifically to work with the fixed palatal TAD-retained anchorage structures or with fixed mandibular TAD-retained anchorage structures.

Variation #5

Aligners in this variation as in variation #3, are designed to use elastic bands to anchor to points in the palate but with this variation the anchor points are attached to a removably engageable palatal anchorage plate that directly engages the palatal TAD's. The removable plate is intended to replace the Wilmes wire framework. The plate has elastic hooks (which can be of various types) to attach the elastics to the aligners. There is no corresponding lower arch two-piece aligner variant.

Again, as in Variation #3, the location of the hooks is determined by the best mechanical advantage to be gained by the force vectors applied by the elastic bands. There will be a space between the plastic of the formed palatal plate and the one-piece maxillary aligner, or between the mandibular aligner and the TAD to allow movement to occur. It can be thought of that in the upper dental arch, essentially the aligner is formed of two separate segments: (A) The TAD engaging palatal segment with elastic hooks, and (B) the tooth covering, arch-shaped segment, also with elastic hooks that connects to the palatal segment with elastic bands, because both of these segments are essentially combined into one segment in Variations #1, 2, and #3. In Variation #4 there is a fixed platform in the palate that is replaced here in Variation #5 by a removable platform.

Variation #6

Aligners in this variation are essentially the same as with variations #4,5 in that there is an aligner that covers the teeth and extends over a portion of the anterior palate, enough so that elastic hooks of various types can be attached including bonded buttons, integrally formed hooks, whether printed or thermoformed, such as can be 3-dimensionally printed, or the border can be shaped in such a way so that a hook is formed, including slots or grooves or specially formed shapes. How far the aligner extends over the palate depends on the desired force vector to be applied to the aligner and the direction the elastic is to be run from the TAD. This variation differs from the other variations in that the elastics will run directly between hooks on the aligners and TAD's that do not require spherical head shapes but will have heads that can support elastic bands. The spherical head shapes should also be able to allow elastics to wrap around them, if they are shaped with a gingival collar to protect the gingival tissue from impingement by the elastic band, they might be usable for the purpose of direct elastic placement.

Variation #7

Aligners in this variation are one piece in design and removably engage the palatally placed TAD's in the maxillary versions or the buccal shelf TAD's in the mandibular versions as in variations #1, 2 and 3. In this variation, there are supporting structures built into the body of the aligner to add strength in certain selected areas. This extra support can come from layering thermoformed aligners to achieve the extra desired strength in the selected area or if the aligner is 3-D printed, then the software can include tools to specify where the additional support structures are to be added. The aligners in this variation can be conventional, or can have loops to connect across interdental spaces, to help open or close these spaces.

Now each of the seven variations will be described in more detail:

Variation #1:

FIG. 1A shows an occlusal view (looking upward from below) of a maxillary dental arch with three TAD's placed in the palate. There is a clear aligner in place over the teeth and the palate.

The posterior border of the aligner can vary in its location depending on the movements of the teeth desired.

Figure 1B:
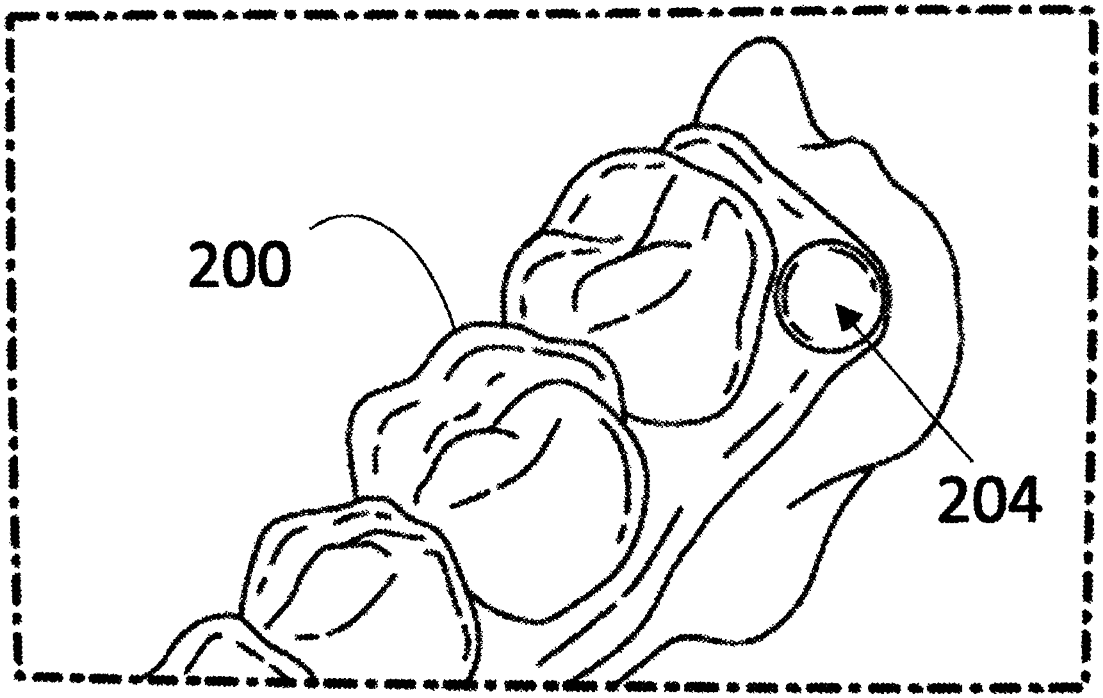
FIG. 1B is a diagram of an example of an aligner placed over a TAD located in the buccal shelf area.

FIG. 1B shows an oblique view of a mandibular dental arch containing teeth to be moved and with a TAD with a spherical head located in the buccal shelf area of the mandible, engaging the flange of an aligner that covers the teeth and the head of the TAD.

Figure 2A:
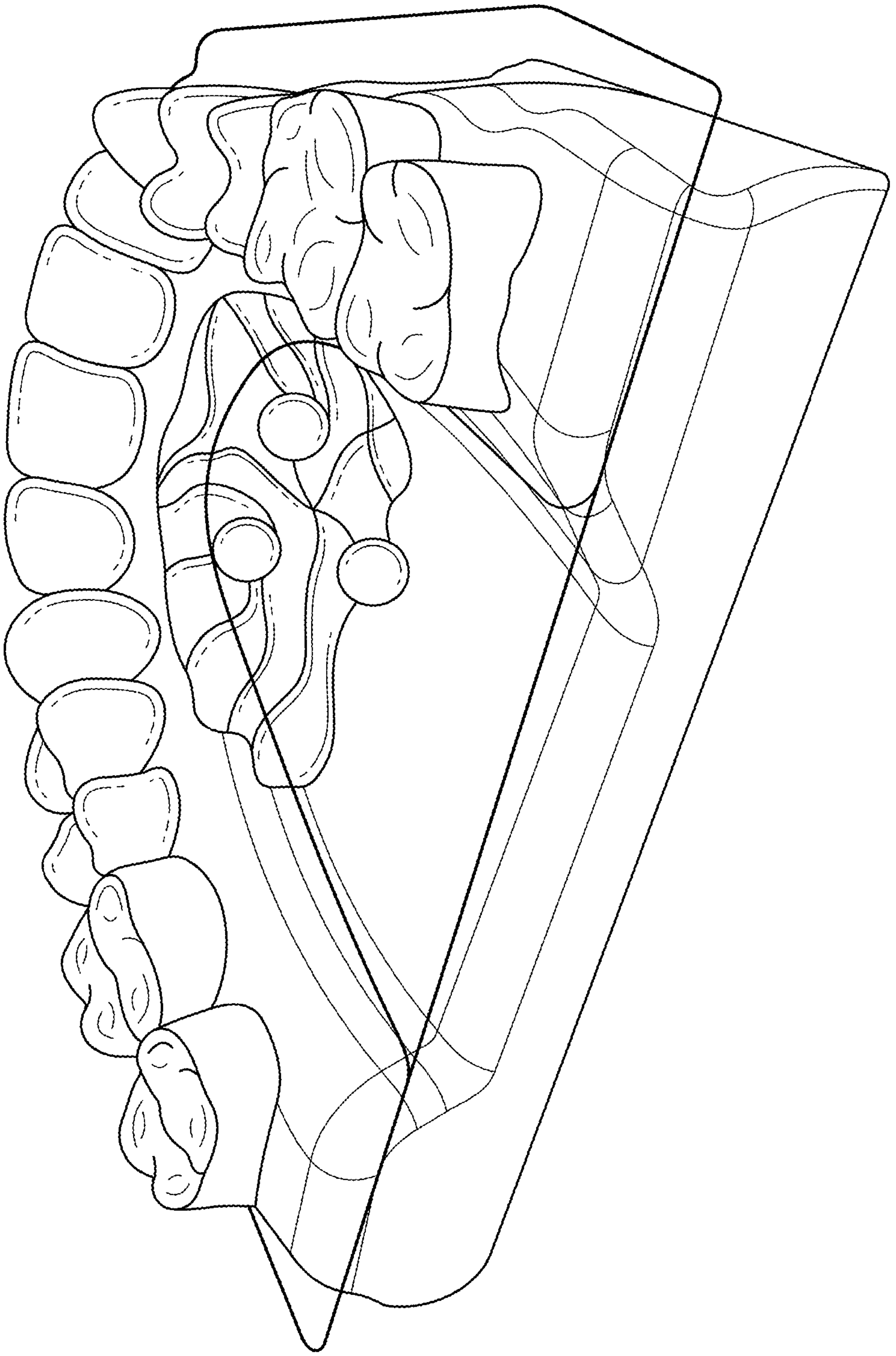
FIG. 2A is a diagram of maxillary arch model illustrating a horizontal cutting plane.

Variation #2:

FIG. 2A shows an oblique view of a maxillary arch model inverted on a table. In this case there is in the software a horizontal cutting plane marking a zone surrounding the palatal TAD's that stays fixed with the TAD's, even if the teeth are moved around it. Alternatively, some other software selection tool that may be more convenient for the user can be utilized to define the zone including the TAD's to be deemed immovable relative to the teeth, or placed into some other software category that may be moved under special circumstances.

Figure 2B:
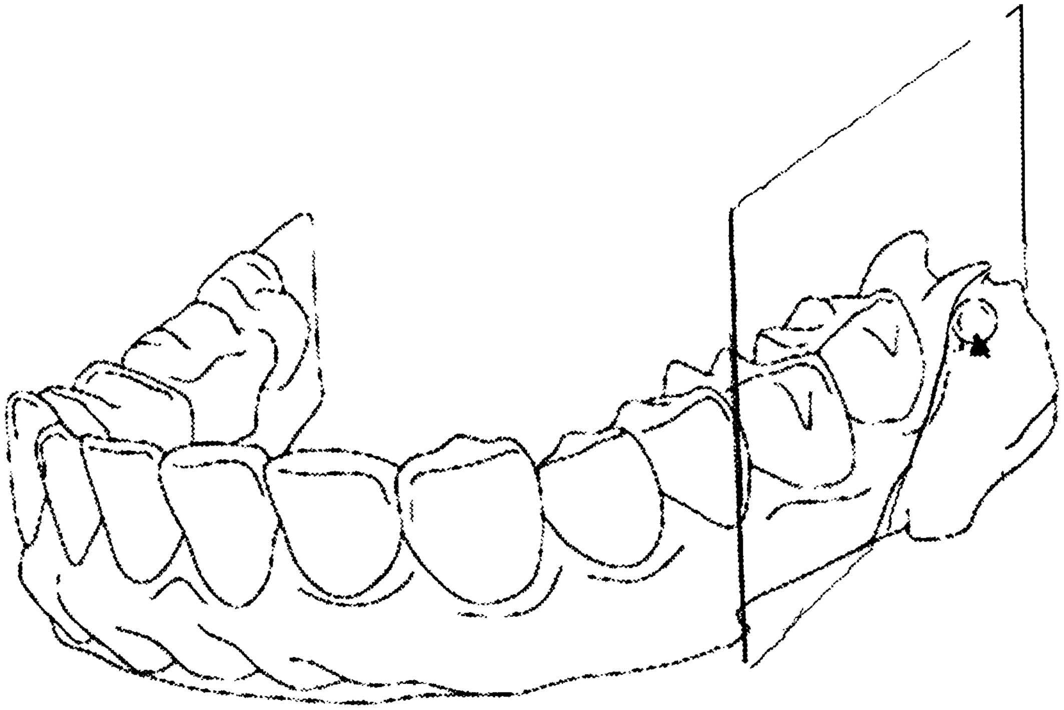
FIG. 2B is a diagram of an example of cutting plane proximate to a TAD located in the buccal shelf area.

FIG. 2B shows an oblique view of a mandibular dental arch similar to that shown in FIG. 2A, but in this case there is a vertical cutting plane marking a zone surrounding the buccal shelf TAD.

Figure 2C:
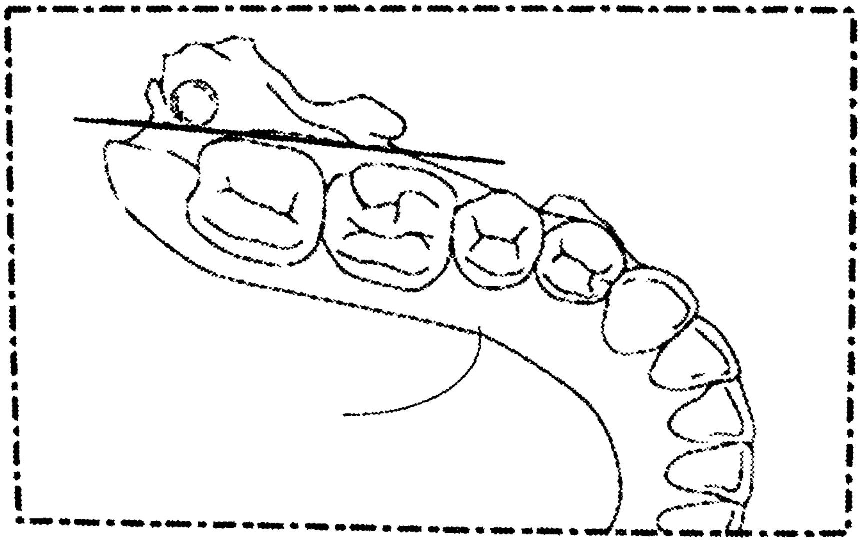
FIG. 2C is a diagram of an example of cutting plane proximate to a TAD located in the buccal shelf area.

FIG. 2C shows an occlusal view looking downward upon of a portion of the same mandibular dental arch model shown in FIG. 2A showing the vertical cutting plane separating the tooth-bearing portion of the model from the lateral portion holding the round TAD.

Variation #3

Figure 3A:
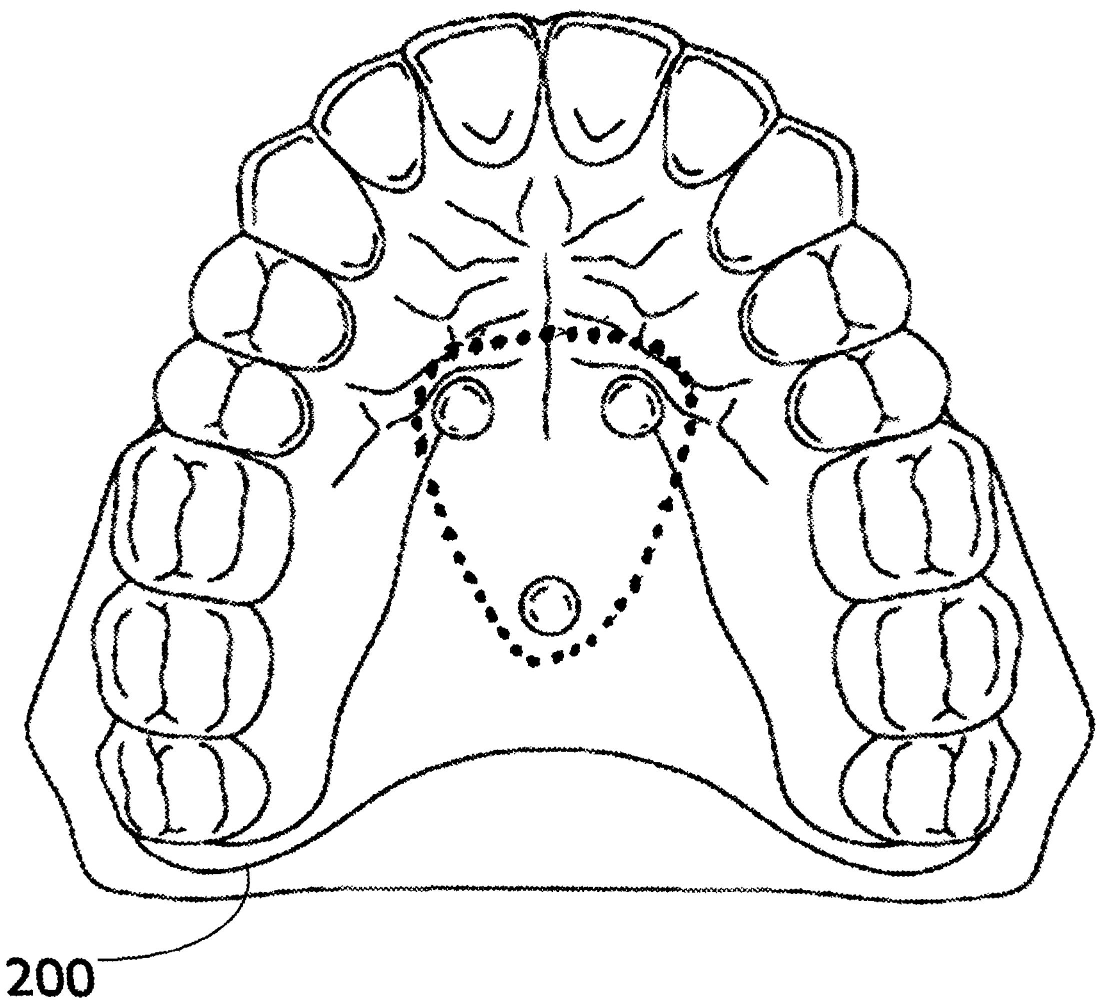
FIG. 3A is a diagram of an example of an aligner placed over the teeth and palate and affixed to temporary anchorage devices with a non-moveable zone.

FIG. 3A shows an occlusal view similar to that shown in FIG. 1, but in this case the software uses a selection tool that can outline the zone indicated here by dotted lines, but can be denoted by any suitable method, around the TAD's, that can be in any reasonable shape or size to indicate the non-movable zone that stays attached to the TAD's.

Figure 3B:
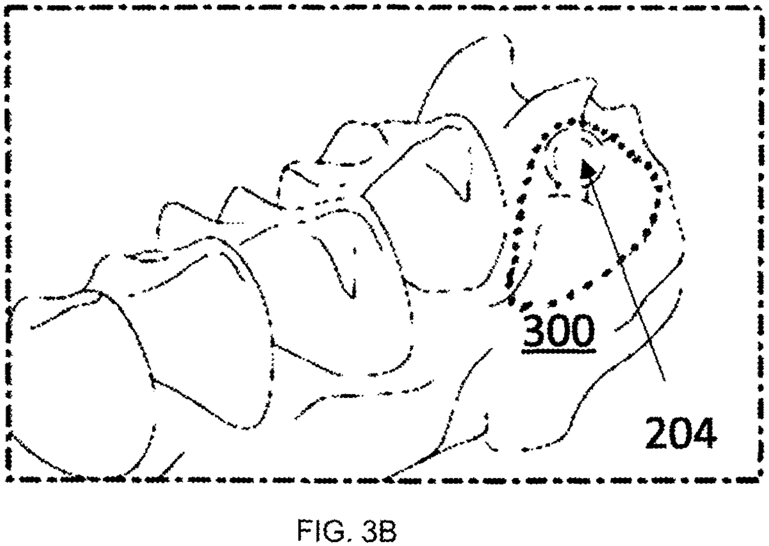
FIGS. 3B-3D are diagrams of an example aligner placed over a TAD located in the buccal shelf area with a non-moveable zone.

FIG. 3B shows an oblique view of a mandibular dental arch similar to that shown in FIG. 2B, but in this case the software uses a selection tool to outline the non-movable zone, indicated by dotted lines, attached to the TAD's positioned on the buccal shelf.

Figure 3C:
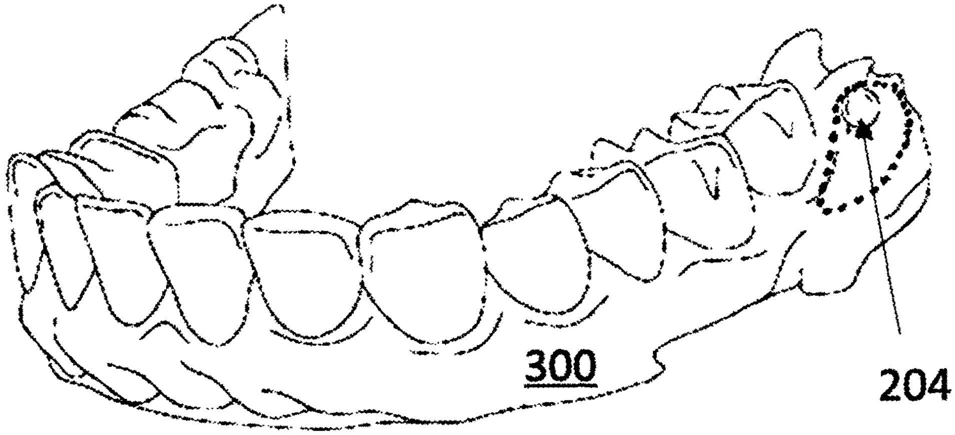
Figure 3D:
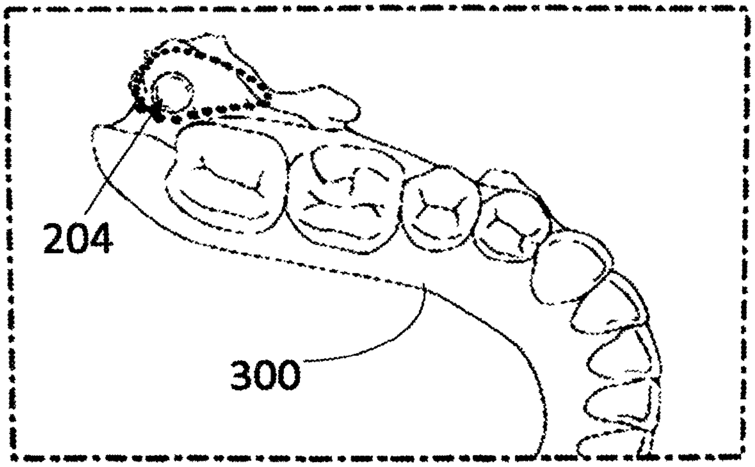

FIGS. 3C and 3D are also views of the same mandibular arch with the TAD and the non-movable zone selected around the TAD indicated by dotted lines.

Variation #4

Figure 4A:
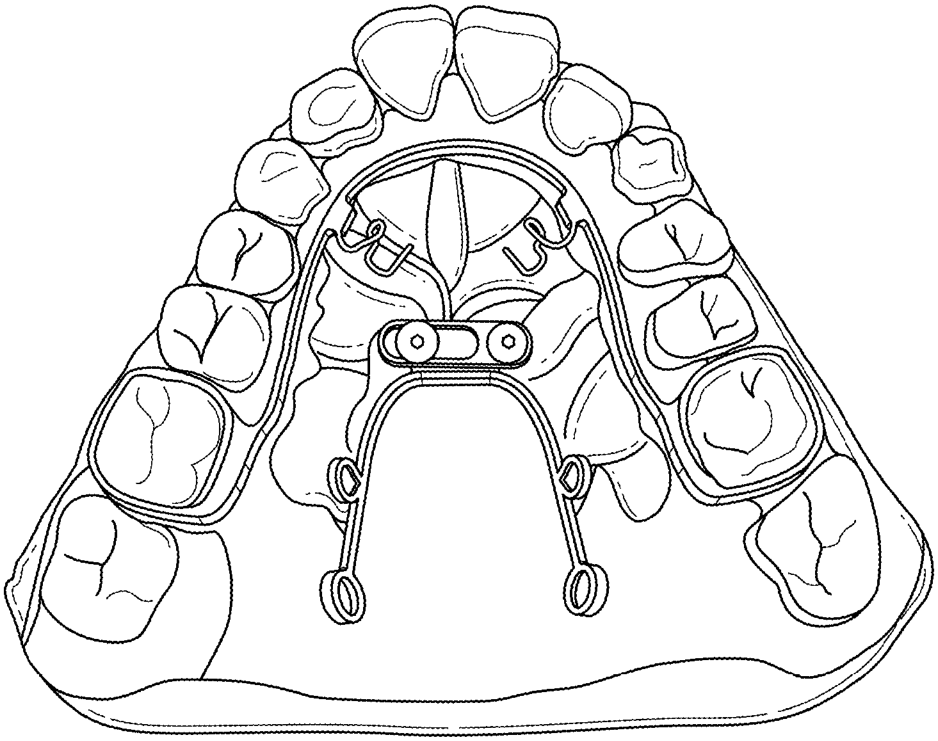
FIGS. 4A-4G are diagrams of an example palatal anchorage screw.
Figure 4B:
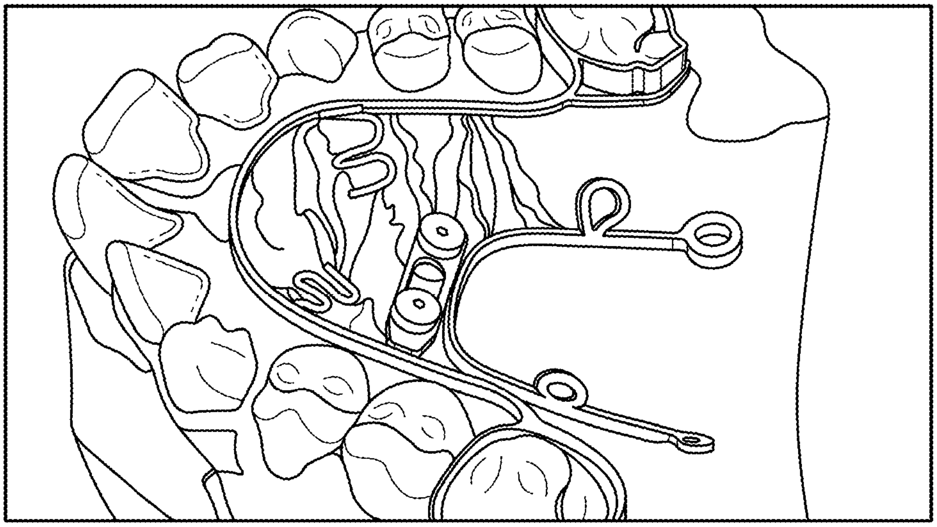

FIGS. 4A and 4B show two views of the palatal anchorage microscrew distalization appliance that was published in the Journal of Clinical Orthodontics, July 2021 article, p. 384 authored by Oronzo De Gabriele, DDS, MD, Ginaluca Dallanta, DT, Sivabalan Vasudavan, BdSc, MdSc, MPH, Benedict Wilmes, DMD, MSD, PhD. The Horseshoe appliance is laser-welded to a "Beneplate," Appliance which is a patented device, registered to Benedict Wilmes.

The inner "Horseshoe anchorage element" held in place by the TAD microscrews in the palate serves as an attachment point for rubber elastic elements to apply forces to move the molar teeth distally which are attached to the soldered stainless steel lingual arch by orthodontic bands.

Figure 4C:
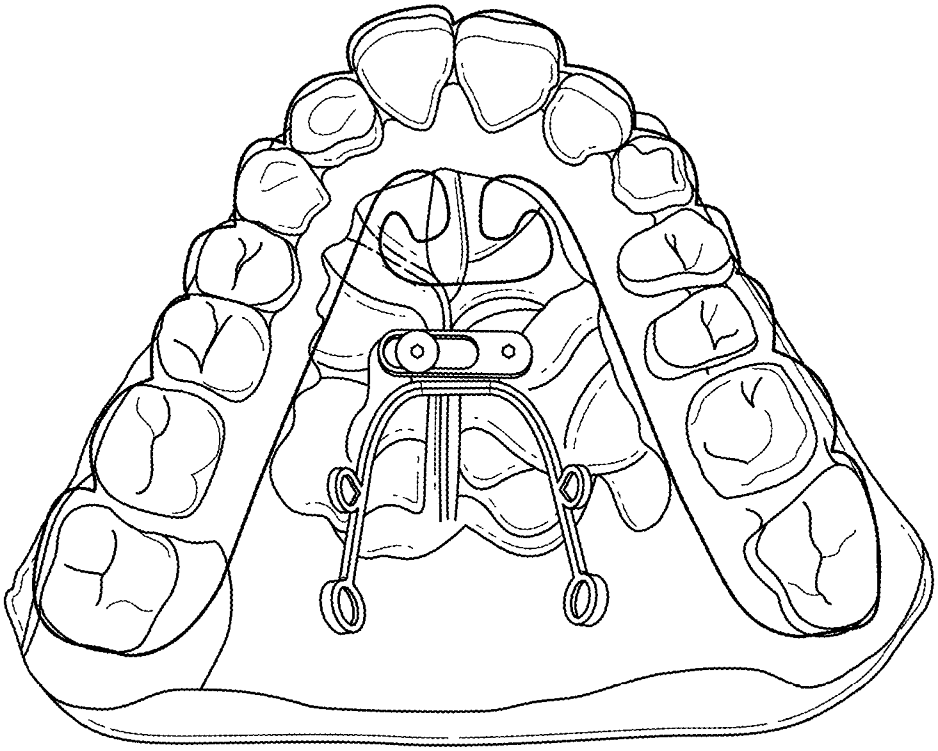
Figure 4D:
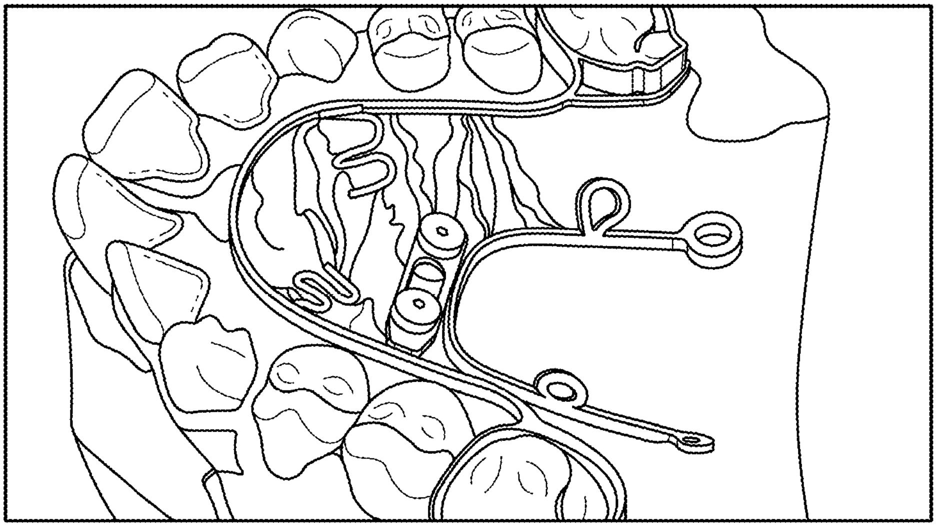
Figure 4E:
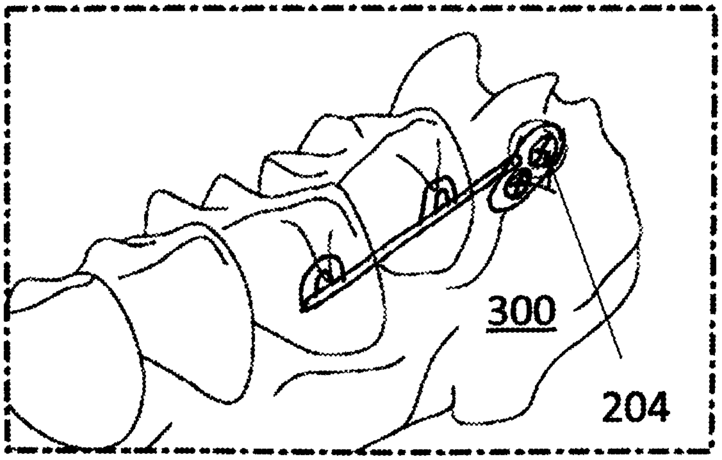
Figure 4F:
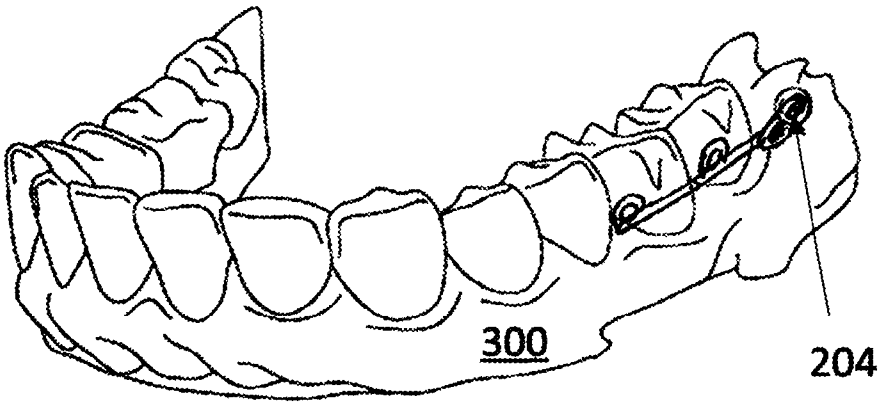
Figure 4G:
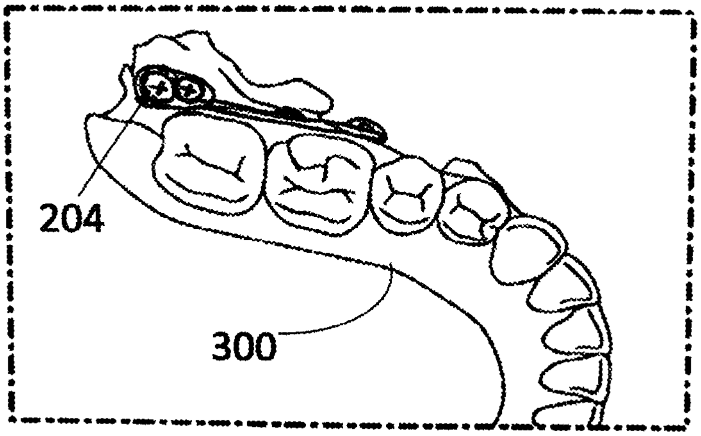

Variation 4 replaces the orthodontic bands and the soldered lingual arch with a removable aligner that fits over the teeth. There are various means whereby hooks can be attached to the aligner for the purpose of engaging elastic bands for force application as in the JCO article picture when the lingual arch is used. In FIG. 4C, the aligner is shown with an anterior palatal lingual border trimmed in such a way so the aligner plastic becomes two hooks for elastics, one on either side of the midline. This "rams-horn" curled hook design has been tested in the mouth and works quite well for holding elastics, lies flat against the palatal tissue, and is non-irritating to the tongue. Other types of elastic hooks that could be used, but are not limited to, include bonded buttons, or slots cut into the border of the aligner at an angle. This FIG. 4C is a modification of the picture from the JCO and shows how the aligner could be used in place of the lingual arch with the Horseshoe Anchorage Element providing the anchorage in the palate. FIG. 4D is a repeat picture of FIG. 4B which is a view from the JCO article of the Horseshoe Distalizer with the lingual arch. FIGS. 4E and 4F are oblique views of a mandibular model of teeth similar to FIG. 6. In this variation the single spherical TAD is replaced by a plate with two holes and two smaller micro TAD's retain the plate in place on the mandibular buccal shelf. A heavy wire or bar is laser welded or soldered to the plate and extends forward horizontally along parallel to the buccal surfaces of the molar teeth. On the bar are attached devices such as loops or hooks to hold elastic bands that will attach on the other end to the lower aligner that fits over the lower teeth. The location of the hooks depends on the forces the operator wishes to apply to the teeth to accomplish the desired tooth movements. In most of the cases where lower arch TAD's will be placed, the purpose is to provide anchorage to allow the posterior teeth to be moved in a distal direction. In many of these cases, elastic bands could be placed directly from the aligner to a TAD placed in the buccal shelf location in the mandible. In cases where the goal is to move the posterior teeth in a mesial direction, the posterior buccal shelf TAD location at the distal third of the second molar, is unfavorable for the use of elastic bands, and that is the motivating need for fabrication of these bars that will attach to TAD's placed on the buccal shelf location. The bar will include loops or hooks that are positioned close to the surface of the aligner in the buccal vestibule in a location far enough mesial to the teeth that need to be moved (as shown here mesial to the first molars). Elastic bands can be removably attached to the loops or hooks on the bars on the mesial end and removably attached to elastic hooks on the aligner at the distal end (not shown in the drawing, but most likely or preferably on the second molar region or whatever tooth, or group of teeth, is desired to be moved in a mesial direction.) The height of the bar will be determined by the operator, depending on the force vectors that are needed to correct the malocclusion presented. The location of the hooks on the aligner, or whether the hooks are placed on the teeth with cutouts placed in the margin of the aligner depends on operator preference. FIG. 4G is an occlusal view looking down from above of the same type of attachment device shown in FIGS. 4E and 4F. The aligner is not shown in these drawings but would be a thin, clear shell covering the teeth, not significantly changing the appearance of the drawing.

Variation #5

As stated earlier, this variation is intended to replace both fixed segments of the "Horseshoe Distalizer" appliance described in the July 2021 JCO article by De Gabriele, et al, with two removable appliance segments, one serving as the palatal anchorage unit and removably engaging palatal TAD's, and the other engaging the teeth, much like a conventional orthodontic aligner. Both of these removable appliance segments will be connected to each other by elastic elements, which could be rubber bands, to apply traction forces in various directions, as designed by the operator.

Figure 5A:
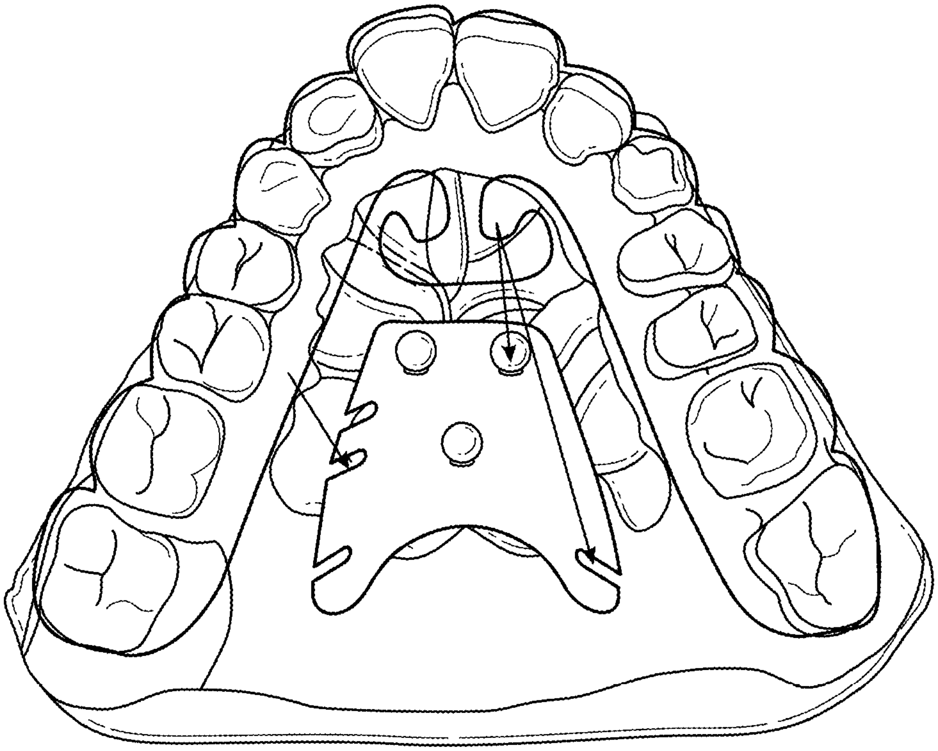
FIGS. 5A-5D are diagrams of an example of a maxillary dental arch with a two-two segment appliance.

FIG. 5A shows an occlusal view of a maxillary dental arch (from below) of the two segments of the appliance: The segment covering the middle of the palate and engaging the three TAD's is outlined in black. On the patient's right side (the left side of the picture) the outline of the palatal anchorage segment shows three rounded notches that could hold an elastic band that will extend forward and will engage at its other end the attachment extension portion of the appliance (i.e., "ram's horn") is configured as an elastic hook notch on the tooth-borne segment of the aligner, thereby applying a force on the entire aligner to move all of the upper teeth, encased in the aligner, in a posterior direction. Only one notch is shown on the palatal anchorage segment on the patient's left side, but more could be added, just as they appear on the patient's right side if the operator desires for them to be utilized. An arrow illustrates where an elastic band could be placed from the anterior "ram's horn" hook to the single notch on the right side of the picture. Alternatively, the elastic band could be removably engaged directly from the "ram's-horn" hook on the tooth supported segment of the aligner directly to one of the bulges formed in the aligner over the palatal TAD's which could serve as an elastic hook if that was the desired force vector. Also shown in this drawing is a possible non-sagittal elastic band placement option on the patient's right side. This force vector would have a vertical component as well as a lateral component and would tend to move the teeth on the patient's left side toward the midline and would tend to intrude the posterior teeth. Obviously, an orthodontic operator has many possible force vectors available with this type of appliance and he/she must be careful how these forces are utilized but it is a powerful tool to correct many types of orthodontic malocclusion problems. Of course, the staging of the movements programmed into the aligner at the point could be designed to move one or more particular teeth in a particular direction, so the force applied by the elastic may not be uniformly applied. In some embodiments, the attachment extension portion may be configured with different shapes such that the attachment extension portion provides for the attachment of elastic bands. The palatal portion of the appliance positioned about the three TADs may have one or more notches or slots about the palatal portion for the attachment of the elastic bands.

Other elastics attachments methods could include bonded buttons or hooks, or if the anchorage segment was 3-D printed an integral hook or attachment means could be printed right into the structure itself.

The shape outline of the palatal anchorage structure shown, the amount of palatal tissue that is covered, the location and number of engaging TADS, the type of TAD's, the shape of the TADS, the shape of the head of the TAD's, the angle of placement of the TAD's, the type, number, and locations of elastic attachment points are all variable, and are all covered by the scope of this patent.

Figure 5B:
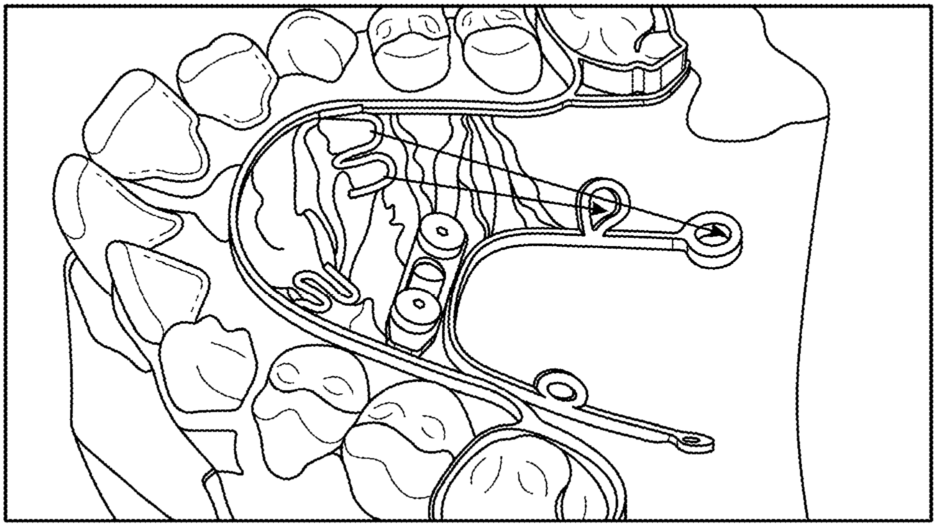

FIG. 5B is a repeat picture of the "Horseshoe Distalizer appliance" from the July 2021 JCO article, just for the sake of comparison. The fixed "Horseshoe Distalizer" is a very effective appliance. The two-segment removable appliance shown in FIG. 5A is very analogous to the "Horseshoe Distalizer," and the forces applied should be comparable both in magnitude and direction, depending on how the operator chooses to place the rubber elastic bands. Possible elastic band attachment location choices are illustrated by the arrows. There are other choices available as well (not shown).

Notice that the fixed molar bands will move the second molar teeth distally first, and then they can be held in place by various means, such as by continuing to apply forces by elastic traction, or stainless steel wire ligatures could be tied to the wire device supported by the TAD's across the space and secured to the hooks on the lingual holding arch cemented to the molar bands.

The molars could then serve as anchors for progressively distalizing the remaining teeth in a serial fashion if fixed braces are applied to the remaining teeth. This is the primary purpose of this device. Alternatively, a clear aligner could be made to fit over the remaining maxillary teeth including the fixed lingual arch with the bands on the second molar teeth after they have been distally moved by the "Horseshoe Distalizer" (with a space appearing mesial to the upper second molar teeth).

Figure 5C:
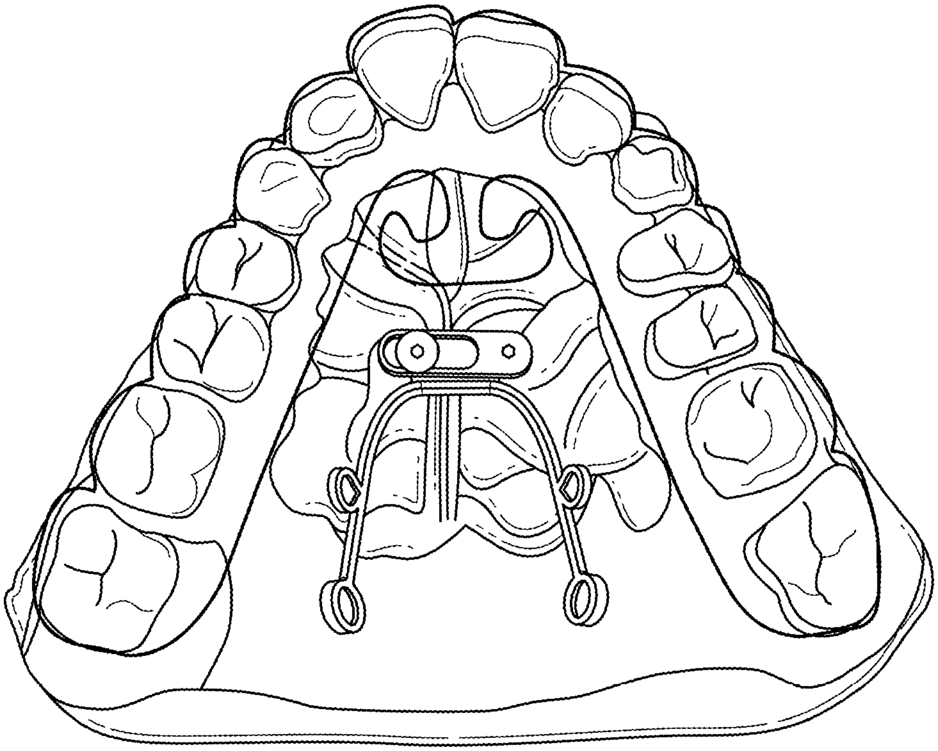
Figure 5D:
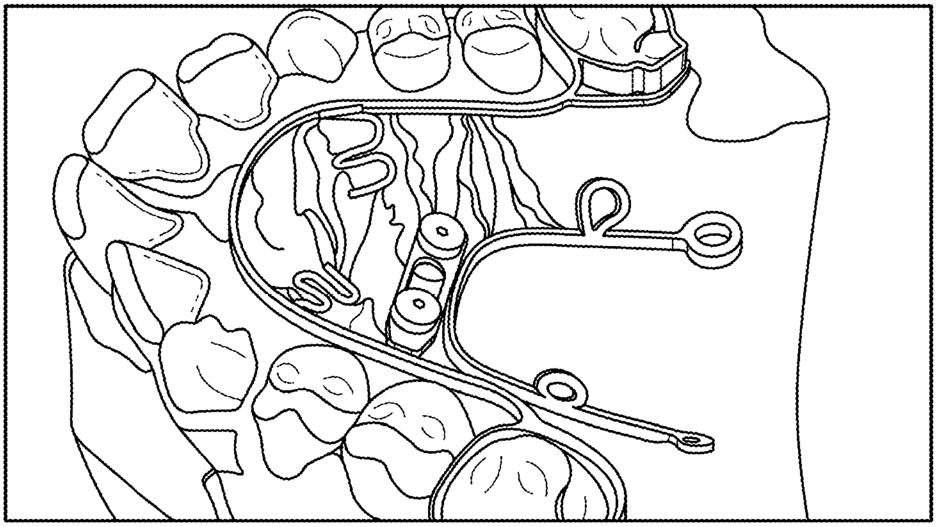

FIG. 5C shows how an aligner with the palatal "ram's horn" hook design could replace the lingual arch with the bands on the second molars but could still work with the palatal inner TAD-retained portion of the "Horseshoe Distalizer" to accomplish the same purpose. FIG. 5D is a repeat of the same picture as shown in FIG. 5B With removable aligners, it is the normal practice to use software to generate a series of "incremental virtual stages" where the teeth are moved short distances, usually a fraction of a millimeter, and then actual 3-D models are fabricated corresponding to these stages, typically by a 3-D printing process, but alternatively the models could be produced by 3-D milling or some other process. Then the aligners are usually fabricated by thermoforming a thin layer of a clear plastic material over the 3-D models, creating a series of aligners. Alternatively, the aligners could also be produced directly by 3-D printing, without first producing a model.

There may be circumstances where it is advantageous to produce, as part of the orthodontic treatment plan, an aligner that is divided into one or more segments, for purposes of anchorage, for superior torque control, or to reduce the number of aligner stages needed.

Figure 5E:
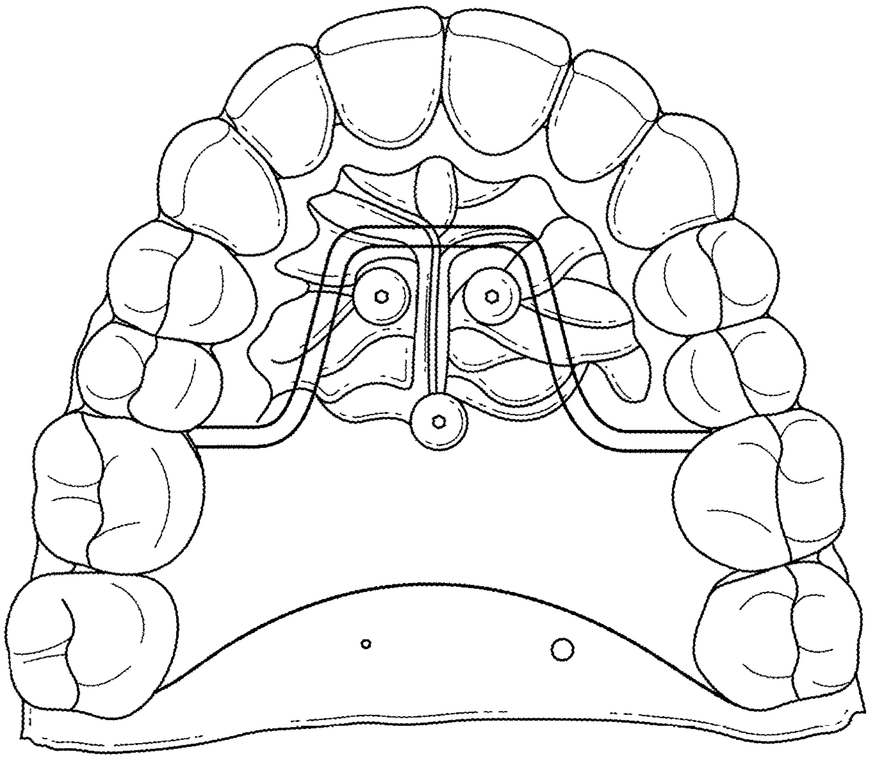
FIG. 5E is a diagram of an example aligner as described herein.
Figure 5F:
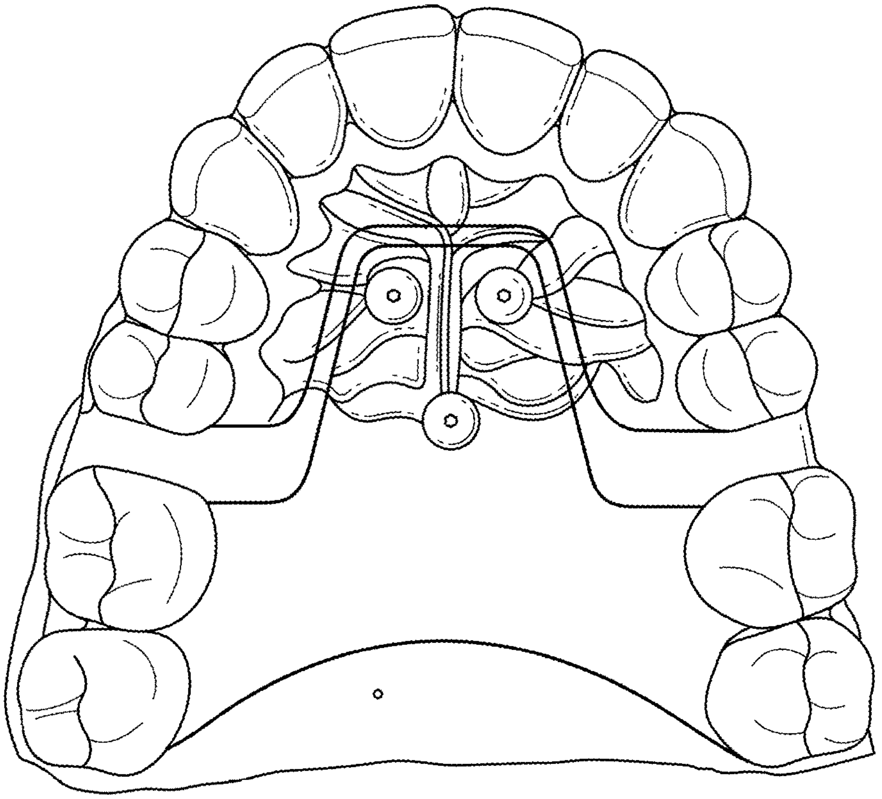
FIG. 5F is a diagram of an example aligner as described herein.

These circumstances may include when significant A-P correction is needed, or when tooth extraction spaces are being closed. They may also include situations where when thermoformed aligners are being used that multiple properties of the thermoformed materials may be needed at the same time. One segment can be made of a thicker material, while another segment can be made of a thinner, more flexible material. Or one segment may need to engage the palatal TAD's for better force delivery, while another segment may be in a holding phase or may not require the use of TAD's at that particular time. FIG. 5E illustrates a possible situation where a two-piece maxillary aligner might be used. The palatal segment engaging the TAD's also includes the posterior palatal portion and the first and second molar teeth. This variation might be used when heavier forces might be needed to accomplish distalizing movements of the large molar teeth in multiple stages, or when uprighting forces are needed. Upper molar teeth are often tipped in a buccal direction. In this variation, even though there are two segments to the appliance, there may or may not be elastics used between the segments, depending on the stage of treatment. FIG. 5F illustrates a possible situation following FIG. 5E when the molars have been recently distalized, and the remaining teeth have not yet been distally moved. The requirements for material thickness may be different between the two segments. A thicker, or stiffer material may be needed to accomplish molar uprighting and distalization while alignment of the anterior teeth may proceed more rapidly with a more flexible material. In the situation shown, where the teeth are fairly well-aligned, then there may not be a motivation for the use of elastics between the segments. In some embodiments, the appliance includes a cut-out section or area between an anterior and posterior portions of the appliance.

Variation #6

Figure 6A:
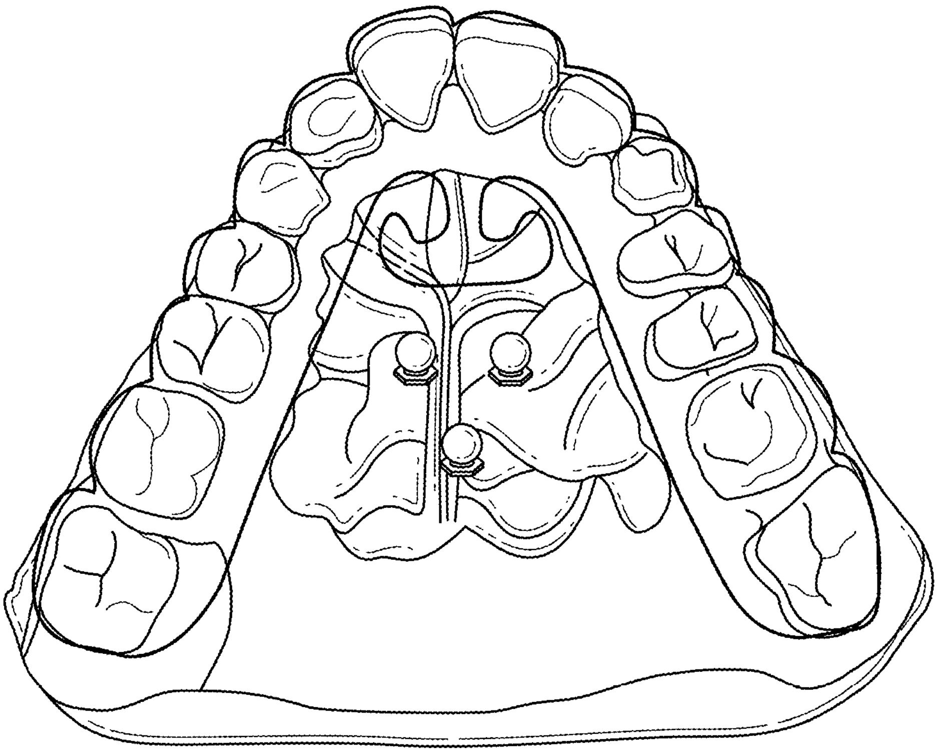
FIGS. 6A-6G are diagrams of example dental appliances as described herein.
Figure 6B:
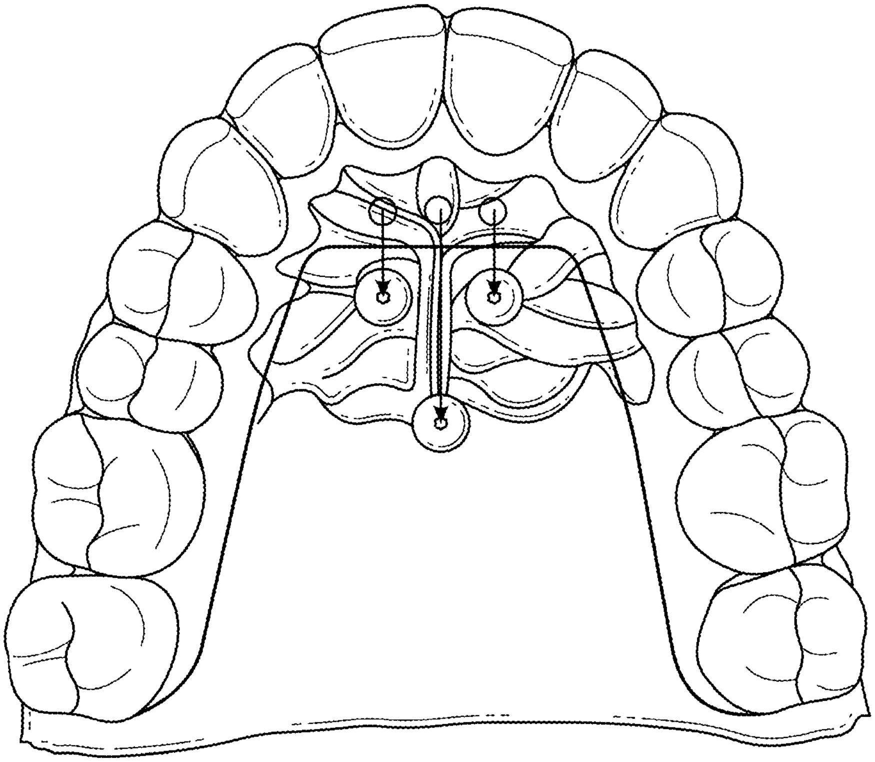

Variation 6 is a one-piece aligner variation covering the teeth and covering the anterior portion of the palate in such a way so that a hook or hooks for the engagement of an elastic band or bands can be attached directly from the aligner to TAD's in the palate in the maxillary variation or from the aligner directly to the buccal shelf TAD's in the mandibular variation. FIG. 6A shows a maxillary aligner with the "Ram's Horn" hook design in the anterior palate. Elastic bands can be attached to the hooks on the "Ram's Horn" and can be run directly to the palatally placed TAD's in various combinations depending on what forces are desired and in what direction. Other types of hooks, including preformed hooks or buttons bonded to the directly to aligner, or cuts could be made in the border of the aligner to form a hook, or if the aligner is directly 3-D printed various hook designs could be printed into the aligner. These hooks could be placed on the maxillary aligner in various places, depending on the direction of forces desired. The placement of the TAD's is shown here in the T-Zone, as per the previously mentioned article published in AJODO by Becker, et al, but other TAD placement options are also possible, especially along the palatal midline where the TAD is still likely to encounter the bony nasal septum and still likely to be stable, as long as it is placed anterior to the posterior nasal spine. FIG. 6B illustrates another variation of the same concept as was shown in FIG. 6A. In 6B small circles represent hooks on the posterior border of the aligner directly behind the upper incisors, and these hooks are placed closer to the teeth than the hooks on the "ram's horn" in 6A. The TAD's are also placed in a more anterior location than in 6A. As previously stated, the hooks on the aligner can be of various designs. The TAD's shown are of a design with a spherical head in keeping with the other disclosures in this application, however in this particular variation, since the TAD's do not engage the aligner directly, the head shape of the TAD's can be of any shape such that a rubber band or elastomeric stretchy element will hook onto it and be retentive without sliding off and also will not allow the elastic element to impinge on the gingival tissues. Many such TAD head shapes for elastic element attachment already exist in the marketplace and include cylindrical designs with flanges at the gingival margins and "nail head" designs to keep the elastic bands from sliding off, mushroom-shaped head designs, outright hooks, etc.

Figure 6C:
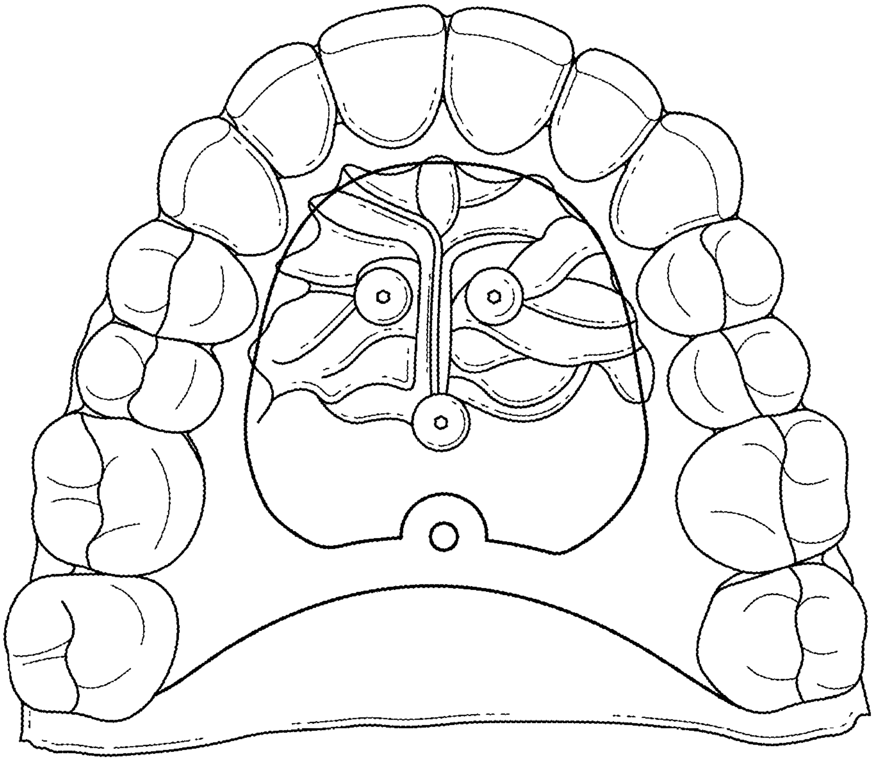
Figure 6D:
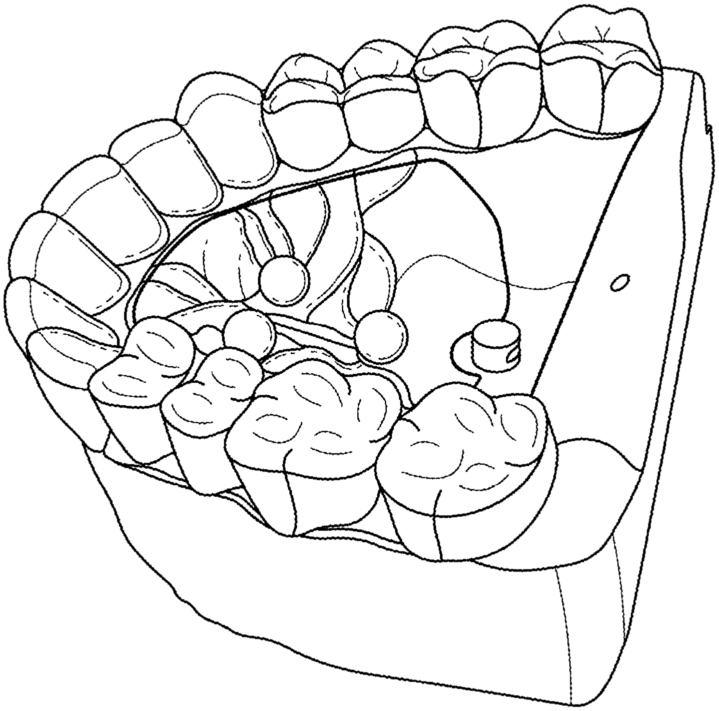

FIG. 6C shows a "reverse" variation with a posterior crossbar extending from left to right across the palate just anterior to the border of the hard and soft palate. It may not be obvious from this illustration, but the palate and the TAD's are not covered by the aligner in this variation. The large ovoid area outlined in black in the illustration is an opening in the aligner, exposing the palate. In the illustration a small circle in the midline of the crossbar is used to represent an elastic hook. An elastic band can be attached from the elastic hook in this posterior location on the aligner going forward to the TAD in the midline, thereby exerting an anterior force on the aligner and the teeth covered by the aligner, such as would be desirable for correction of an Angle Class III malocclusion. Although only one elastic hook is shown in this illustration, it is to be understood that multiple hooks could be used with multiple elastic bands applying forces, possibly to multiple TAD's, depending on needs of the case being treated and the treatment plan of the orthodontist. FIG. 6D is a perspective view of an upper dental arch model with an aligner of the same "reverse" type as was shown in FIG. 6C. Because of the point of view, the patient's right side portion of the posterior palatal crossbar is not shown because it is hidden behind the right side upper first and second molars. A vertical cylindrical projection with a posterior cut-out to serve as a hook to retain the posterior end of a stretchy elastic band is shown attached in the center of the posterior palatal crossbar. The other end of the elastic band would be attached directly to a palatal TAD, most likely in the midline. Alternatively, some combination of bands could be used or, for example, a longer band could be attached to both of the two anterior TAD's shown on this model, and folded around the elastic hook attached to the aligner posterior crossbar. This is only one example of many possible hook designs that could potentially be utilized to support elastic bands that could be used to hook directly from aligners to TAD's. As mentioned earlier, bonded hooks or buttons are commercially available for this purpose. Slots can be cut into the edge of aligners to support elastic bands. If aligners are directly 3-D printed, then hooks can be formed directly into the design of the printed aligners as they are printed.

Figure 6E:
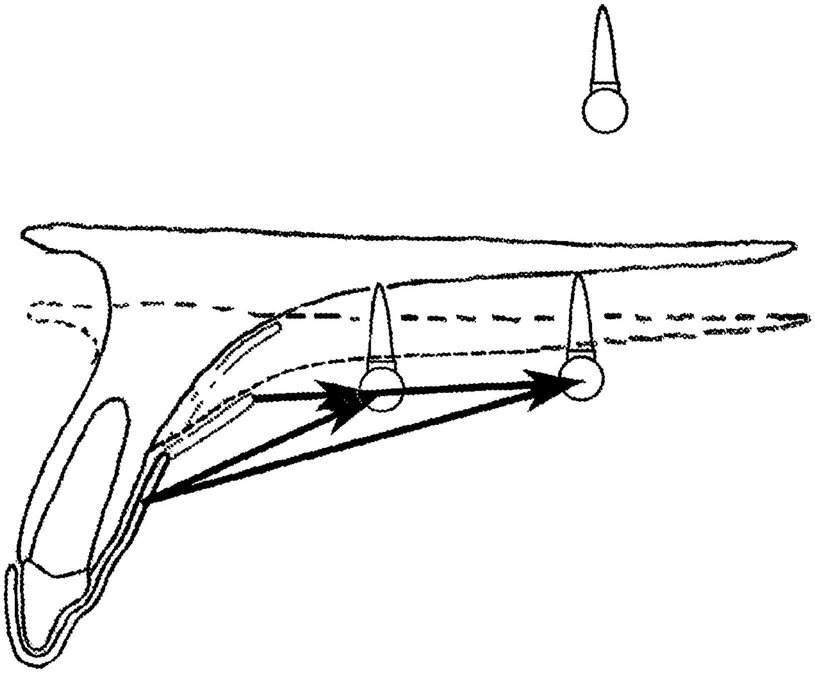
Figure 6F:
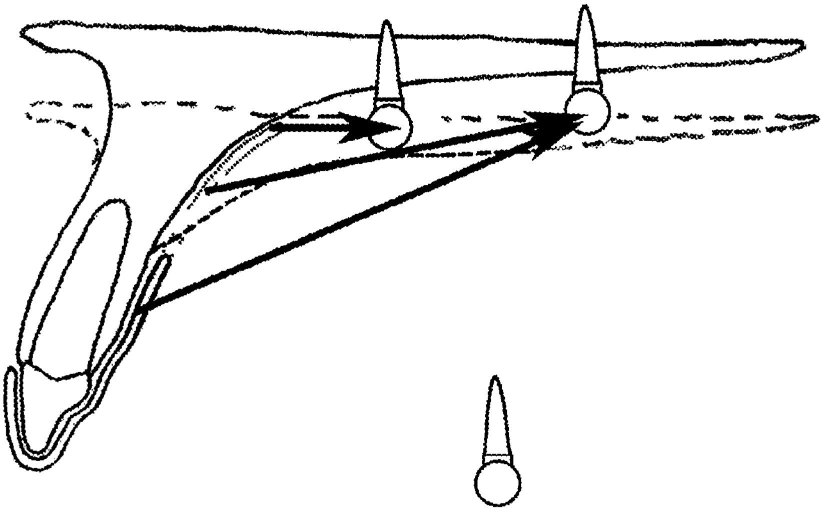

The vertical dimension of the maxilla varies from person to person, and one vertical dimension of particular relevance to TAD's and aligners is the vertical height of the alveolar process, the bony housing that surrounds the teeth, seen in a cross-sectional view of a portion of the maxilla in FIGS. 6E and 6F relative to the horizontal palatine process. A solid outline of a tall bony maxilla is shown. A shorter maxilla is shown superimposed with a dashed line. We would say the taller maxilla has a "deep palate" and the shorter maxilla has a "shallower palate."

FIG. 6E shows possible force vectors originating from a point along the lingual surface of the aligner close to the incisor teeth, extending back toward a TAD placed toward the center of the palate with the shorter vertical dimension, and a slightly more horizontal force vector directed toward a TAD placed more posteriorly. As depicted, bands may be attached to one or more attachment portions of the dental appliance and to one or more TADs. Note that a nearly horizontal force vector can be achieved by extending the anterior aligner hook farther posteriorly and higher into the palate to a level approximately equal to that of the TAD's. A greater range of activation can be achieved by placing the TAD in a more posterior position, farther away from the hook on the aligner.

Likewise, FIG. 6F shows TAD's placed in the maxilla with the taller dimension. Vector forces are shown originating from the lingual surface of an aligner from three different possible vertical locations, directed toward one or the other of two possible palatal TAD's. Again note that nearly horizontal force vectors are possible, if the aligner is extended far enough into the palate to match the vertical height of the TAD's, and the range of activation can vary depending on the location of the TAD relative to the hook on the aligner, shown here in cross-section, in both solid and dotted lines, depending on the desired palatal extension and force vectors.

Figure 6G:
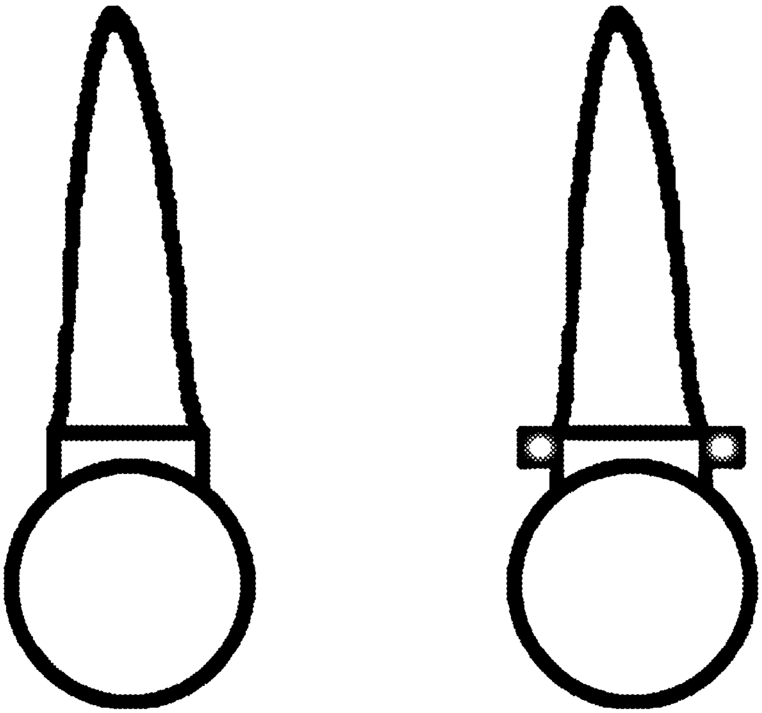

For direct placement of elastic bands to the TAD's, it is desirable to place TAD's that have a gingival collar to prevent the elastic band from sliding into the palatal tissue and causing irritation. Alternatively, a TAD with a hook design that holds the elastic band away from the tissue is acceptable. FIG. 6G shows a cross-sectional view of a TAD (minus the screw threads on the shank) with and without a gingival collar just to illustrate the concept or the idea of a flange on the TAD to prevent an elastic band from sliding into the gum tissue. In the previous variations discussed in this disclosure, TAD's without gingival collars are shown and are sufficient to engage the aligners directly.

Variation #7

Variation 7 is also a one-piece aligner design like variations 1, 2, 3, and it directly engages palatal TAD's in the maxilla and buccal shelf TAD's in the mandibular version. It differs from the earlier variants in that it has supporting structures built into the body of the aligner to add strength in certain selected areas where the extra strength may be required to better perform certain functions. These structures can be simply extra thickness applied to specific areas, such as adding (an) additional layer(s) to a thermoformed aligner, or it can be a printed zone in a printed aligner that is thicker, or it can be more complex, such as a printed strut, beam, or ridge with a specified cross-section. It can also be a supporting structure that is attached at both ends to the aligner but is disconnected from the body of the aligner throughout much of its length, such as a supporting arch.

Figure 7A:
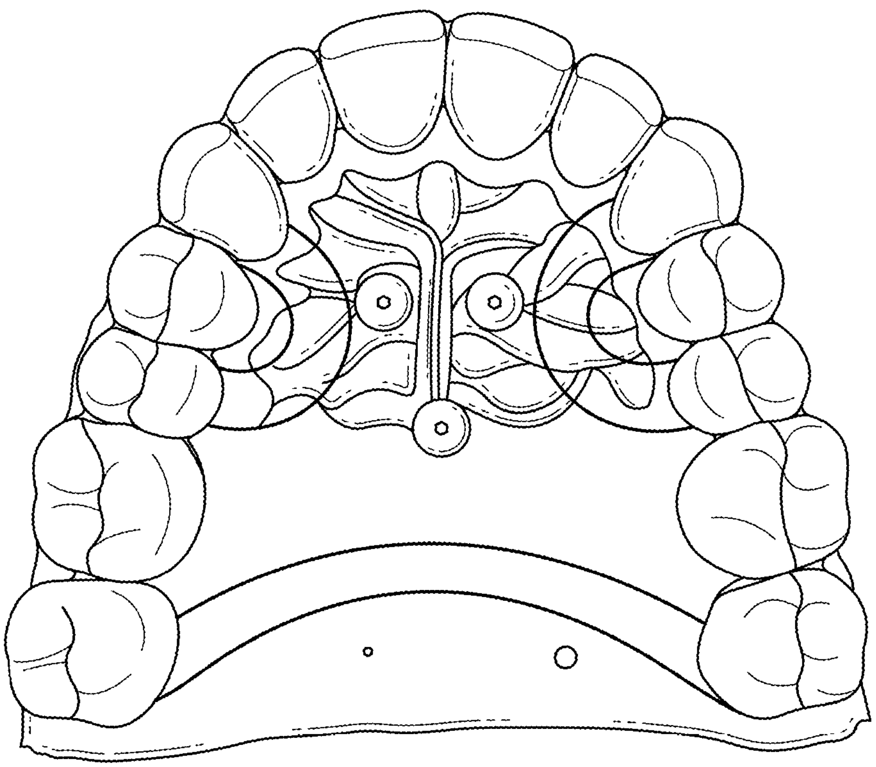
FIG. 7A-7B are diagrams of an example aligner as described herein.

FIG. 7A shows an occlusal view (from below) of an upper 3-D printed model of teeth with a clear aligner in place. The black lines indicate regions where there is extra thickness for extra support, in this case provided by an extra layer of clear thermoformed material. The posterior border area connecting the upper second molars has been made thicker because upper second molar teeth often have the crowns of the teeth tipped laterally, in a buccal direction, and they need to be moved to a more vertically upright position. The additional aligner thickness helps to provide additional strength to the aligner to support this needed corrective movement. The appliance may be made with areas of additional thickness to provide strength and rigidity for those portion of the appliance where the appliance does not have a portion of the appliance that seats over a tooth FIG. 7A also shows that the upper first premolars have been removed (in this case, by covering that portion of the image with a mask). As part of the orthodontic treatment plan, the extraction spaces are to be closed. The teeth adjacent to the extraction sites will be the teeth that need to move the most in order to close the spaces, and these teeth will have a strong tendency to tip into the spaces as the spaces are being closed. A series of aligners will be made to close the spaces, each with the spaces slightly more closed than the previous aligner. To counteract the tipping tendency, bonded attachments can be placed on the teeth to improve the ability of the aligners to engage the teeth as they are being moved. The shape of the bonded attachments can take many forms, including rectangular and wedge designs which have been used for many years in the industry. FIG. 7A shows a semi-circular support structure placed around the extraction site, providing additional support for the teeth adjacent to the extraction site, to help prevent tipping and to help provide force to help close the space.

Figure 7B:
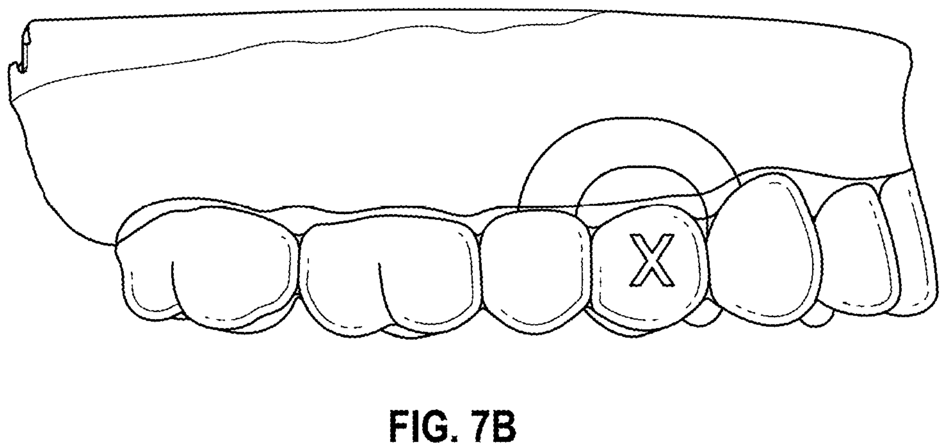

FIG. 7B is a side view of a 3-D printed model of maxillary teeth with a clear aligner in place.

Light-colored markings indicate by an "X" where the first premolar extraction is to take place.

The light-colored arch outlines an arch shape that is a U-shape connector element joining the teeth adjacent to the extraction site. Similar U-shaped connecting elements were described in previous patents filed by Martz, et al, including the filing on Aug. 25, 2022, but the purpose of the previous U-shaped connector in the previous was to make the aligner more flexible. The purpose of the U-shaped connector here is to provide more support on the facial side, while the semi-circular support on the lingual side is also to provide more support. This support could be thermoformed in one or more layers on the facial side, but it could also be 3-D printed, and therefore need not be flat in cross-section the way it would be if it were thermoformed from sheet stock. The cross-section could be round, diamond-shaped, I-beam shaped, or any cross-section that is suitable.

The support structures are by no means limited to the examples shown. They could run longitudinally to provide a backbone of support to help provide more stiffness to the aligner to help correct the Curve of Spee, or to reduce the incisor overbite, or to provide support rails for elastics in almost any location where extra support is felt to be needed.

They need not be confined to the palatal or lingual side of the aligners. They could be placed transversely to aid with arch expansion. With 3-D printed aligners, many more justifications for support are likely to find applications . . . Class II correctors, intrusion appliances, support points for elastics, or ligatures for TAD's for orthognathic surgery applications, etc.

Figure 7C:
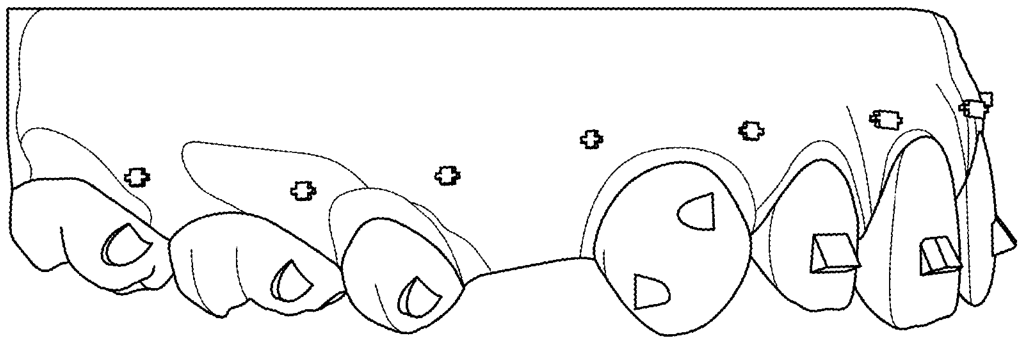
FIG. 7C is a diagram of example of a user interface depicting a model of maxillary teeth having bonded attachments placed the teeth.

FIG. 7C shows a lateral view in the ArchForm® software of a set of maxillary teeth with an upper right first premolar extracted. There are bonded attachments placed on all of the teeth. The purpose of the attachments is to enhance the connection of the aligner to the tooth, to enable the aligner to apply controlled forces to move not only the crowns of the teeth, but also root movements, following the orthodontist's treatment plan.

These are not the only type of attachments that could be used in this case. Many other attachment combinations could be used including rectangular attachments, that have been used successfully for extraction cases in the past. This is just one illustration. Bonded attachments were not shown in FIG. 7B, but closing the extraction space would be much more likely to be successful, with less tipping of teeth occurring if bonded attachments are used.

Figure 7D:
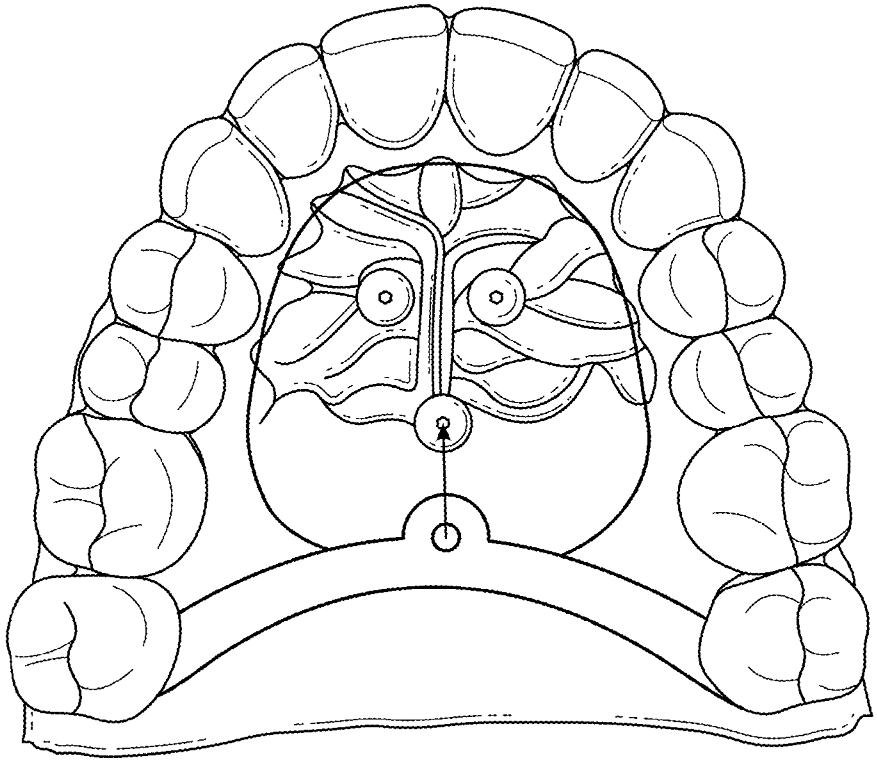
FIG. 7D is a diagram of an example aligner as described herein.

FIG. 7D is another example of an aligner with a reinforced section. This is a "reverse" aligner almost identical to that shown earlier in FIGS. 6B and 6C, with a posterior palatal crossbar and an ovoid anterior palatal cutout region that does not directly engage the TAD's. The difference between this aligner and the one shown earlier in 6B and 6C is the posterior palatal crossbar is reinforced, either by layering with multiple layers if the aligner is made by thermoforming, or by printing with extra thickness or with some type of 3-dimensional surface strengthening structure such as a ridge or bar. It has been mentioned earlier that if thermoformed, a surface structure could be formed into the palate, such as a ridge or a v-shaped, or rounded projecting elongated elevation to make the thermoformed material less flexible in this area. The purpose is to give the aligner greater strength in this upper molar area, where the molar crowns are often tipped buccally prior to treatment.

Figure 8:
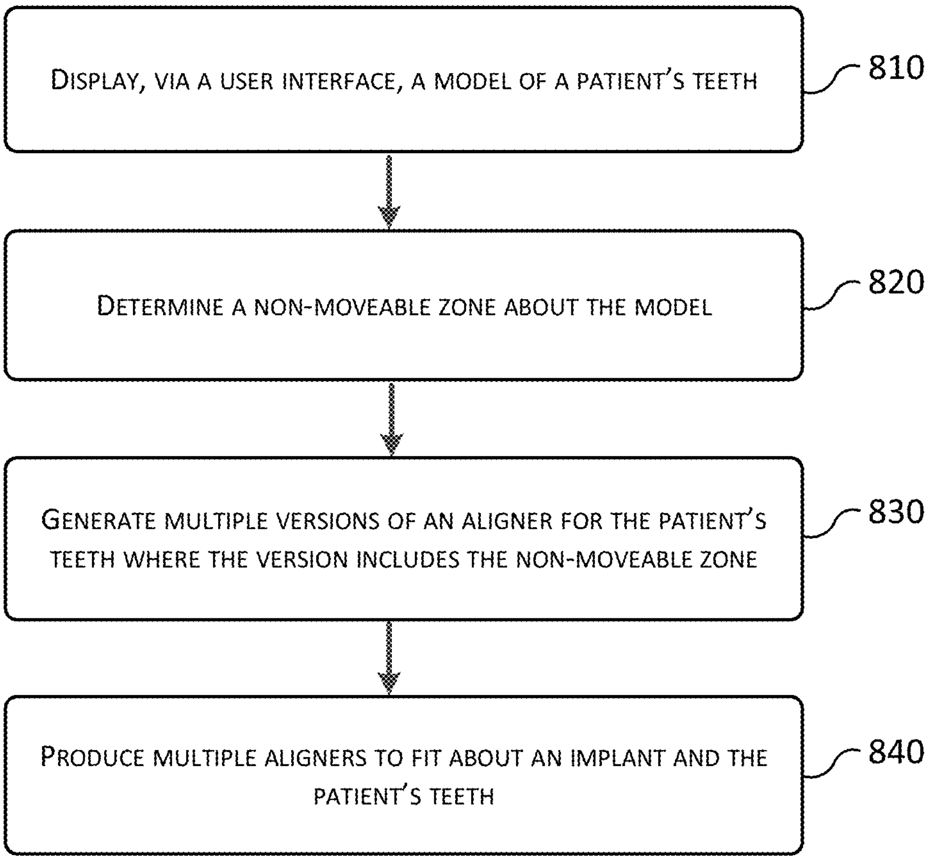
FIG. 8 illustrates a flowchart of a method used to design an aligner.

FIG. 8 illustrates a flowchart of a method used to design and produce aligners to fit over an implant and a patient's teeth. In some embodiments, a computer system provides a process 800 to add non-moveable zones to a model of a patient's teeth about one or more implants.

In step 810, the system may display a user interface displaying a model of a patient's teeth and the patient's palate and/or the buccal shelf area. The palate and/or the buccal shelf area may include one or more depicted implants. For example, the models of the figures may be displayed via a user interface.

In step 820, the system, determines a non-moveable zone about the model. The user interface may receive a user input for the selection of an area about the model designating a portion of the model non-moveable zone. For example, the user interface may provide input controls allowing a user to draw or select boundary areas about the model. The input controls allow for size and movement about the user interface.

The non-moveable zone may be geometrically aligned with the one or more implants. For example, the non-moveable zone may be associated or anchored to an implant so that the non-moveable zone has a fixed location as to an implant in the model. The non-moveable zone may be attached or anchored to one or more implants depicted as part of the model. The user interface may display the non-moveable zone as a border encompassing the one or more implants and/or a horizontal line or plane. The horizontal line or plane may depict a cutting plane as to an aligner and may define regions around the one or more implants that are immoveable.

In step 830, the system may generate multiple electronic versions of aligner models, schematics or templates where successive versions of aligners are used to move the patient's teeth. The system may generate multiple versions of aligners that are configured to fit over the one or more implants and the patient's teeth. The aligners provide for movement of the patient's teeth to successive versions of the aligner. The areas of the aligner that were identified as a non-moveable zone that remains in a fixed location relative to aligner body portions that are adjusted to cause the movement of the patient's teeth.

In step 840, the system may instruct another system to produce multiple aligners to fit about the patient's teeth and the one or more implants. Also, the system may generate electronic files with schematics for use in producing a physical series of aligners. The aligners have portions of material that would fit over and provide a fitment over attachments as depicted in the model of the patient's teeth. For example, the implants may include any one of a temporary anchorage device or a palatal anchorage appliance.

Figure 9:
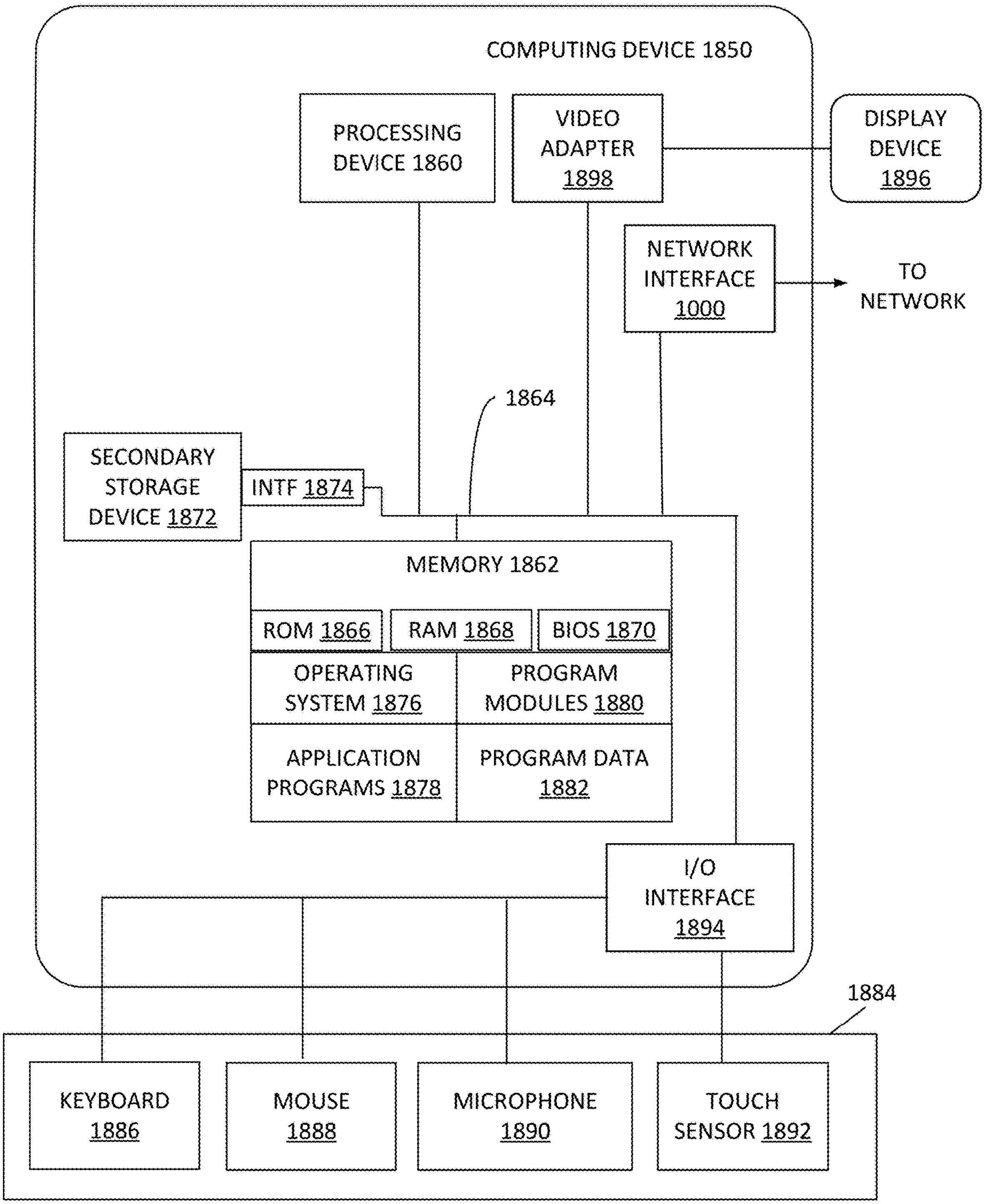
FIG. 9 shows an example of a computer device that may be used in the design and fabrication of the dental appliances described herein.

FIG. 9 shows an example of a computer device that may be used in the design and fabrication of the dental appliances described herein. For example, the computer device may be used to design an aligner or a series of aligners that include at least some of the functionality described herein. In this example architecture, a computing device 1850 can be used to implement aspects of the present disclosure, including methods of planning treatments, designing thin-shell aligners, fabricating thin-shell aligners, and placing attachments for the flexible segments on digital representations of thin-shell aligners.

The computing device 1850 illustrated in FIG. 10 can be used to execute the operating system, application programs, and software modules (including any software engines) described herein.

The computing device 1850 includes, in some embodiments, at least one processing device 1860, such as a central processing unit (CPU). A variety of processing devices are available from a variety of manufacturers, for example, Intel or Advanced Micro Devices. In this example, the computing device 1850 also includes a system memory 1862, and a system bus 1864 that couples various system components including the system memory 1862 to the processing device 1860. The system bus 1864 is one of any number of types of bus structures including a memory bus, or memory controller; a peripheral bus; and a local bus using any of a variety of bus architectures.

Examples of computing devices suitable for the computing device 1850 include a desktop computer, a laptop computer, a tablet computer, a mobile computing device (such as a smart phone, an iPod® or iPad® mobile digital device, or other mobile devices), or other devices configured to process digital instructions.

The system memory 1862 includes read only memory 1866 and random-access memory 1868. A basic input/output system 1870 containing the basic routines that act to transfer information within computing device 1850, such as during start up, is typically stored in the read only memory 1866.

The computing device 1850 also includes a secondary storage device 1872 in some embodiments, such as a hard disk drive, for storing digital data. The secondary storage device 1872 is connected to the system bus 1864 by a secondary storage interface 1874. The secondary storage devices 1872 and their associated computer readable media provide non-volatile storage of computer readable instructions (including application programs and program modules), data structures, and other data for the computing device 1850.

Although the example environment described herein employs a hard disk drive as a secondary storage device, other types of computer readable storage media are used in other embodiments. Examples of these other types of computer readable storage media include magnetic cassettes, flash memory cards, digital video disks, Bernoulli cartridges, compact disc read only memories, digital versatile disk read only memories, random access memories, or read only memories. Some embodiments include non-transitory computer-readable media. Additionally, such computer readable storage media can include local storage or cloud-based storage.

A number of program modules can be stored in secondary storage device 1872 or system memory 1862, including an operating system 1876, one or more application programs 1878, other program modules 1880 (such as the software engines described herein), and program data 1882. The computing device 1850 can utilize any suitable operating system, such as Microsoft Windows™, Google Chrome™ OS or Android, Apple OS, Unix, or Linux and variants and any other operating system suitable for a computing device. Other examples can include Microsoft, Google, or Apple operating systems, or any other suitable operating system used in tablet computing devices.

In some embodiments, a user provides inputs to the computing device 1850 through one or more input devices 1884. Examples of input devices 1884 include a keyboard 1886, mouse 1888, microphone 1890, and touch sensor 1892 (such as a touchpad or touch sensitive display). Other embodiments include other input devices 1884. The input devices are often connected to the processing device 1860 through an input/output interface 1894 that is coupled to the system bus 1864. These input devices 1884 can be connected by any number of input/output interfaces, such as a parallel port, serial port, game port, or a universal serial bus. Wireless communication between input devices and the interface 1894 is possible as well, and includes infrared, BLUETOOTH® wireless technology, 802.11a/b/g/n, cellular, ultra-wideband (UWB), ZigBee, or other radio frequency communication systems in some possible embodiments.

In this example embodiment, a display device 1896, such as a monitor, liquid crystal display device, projector, or touch sensitive display device, is also connected to the system bus 1864 via an interface, such as a video adapter 1898. In addition to the display device 1896, the computing device 1850 can include various other peripheral devices (not shown), such as speakers or a printer.

When used in a local area networking environment or a wide area networking environment (such as the Internet), the computing device 1850 is typically connected to the network through a network interface 1000, such as an Ethernet interface or WiFi interface. Other possible embodiments use other communication devices. For example, some embodiments of the computing device 1850 include a modem for communicating across the network.

The computing device 1850 typically includes at least some form of computer readable media. Computer readable media includes any available media that can be accessed by the computing device 1850. By way of example, computer readable media include computer readable storage media and computer readable communication media.

Computer readable storage media includes volatile and nonvolatile, removable and non-removable media implemented in any device configured to store information such as computer readable instructions, data structures, program modules or other data. Computer readable storage media includes, but is not limited to, random access memory, read only memory, electrically erasable programmable read only memory, flash memory or other memory technology, compact disc read only memory, digital versatile disks or other optical storage, magnetic cassettes, magnetic tape, magnetic disk storage or other magnetic storage devices, or any other medium that can be used to store the desired information and that can be accessed by the computing device 1850.

Computer readable communication media typically embodies computer readable instructions, data structures, program modules or other data in a modulated data signal such as a carrier wave or other transport mechanism and includes any information delivery media. The term "modulated data signal" refers to a signal that has one or more of its characteristics set or changed in such a manner as to encode information in the signal. By way of example, computer readable communication media includes wired media such as a wired network or direct-wired connection, and wireless media such as acoustic, radio frequency, infrared, and other wireless media. Combinations of any of the above are also included within the scope of computer readable media.

The computing device illustrated in FIG. 9 is also an example of programmable electronics, which may include one or more such computing devices, and when multiple computing devices are included, such computing devices can be coupled together with a suitable data communication network so as to collectively perform the various functions, methods, or operations disclosed herein.

It will be appreciated that the present disclosure may include any one and up to all of the following examples below and their combinations.

Example 1: A method of creating an orthodontic appliance: displaying, via a user interface, a model of a patient's teeth and the patient's palate and/or the buccal shelf area, wherein the palate and/or the buccal shelf area depict one or more implants; determining a non-moveable zone about the model; and generating multiple versions of an aligner configured to fit over the one or more implants and the patient's teeth, wherein the patient's teeth have movement with regard to successive versions of the aligner and as the non-moveable zone that remains in a fixed location.

Example 2: The method of Example 1, wherein the implants comprise any one of a temporary anchorage device or a palatal anchorage appliance.

Example 3: The method of any one of Examples 1-2, wherein the determining a non-moveable zone about the model comprises: receiving a user input for the selection of an area about the model designating a portion of the model non-moveable zone.

Example 4: The method of any one of Examples 1-3, wherein the non-moveable zone is depicted, via the user interface, as a border encompassing the one or more implants.

Example 5: The method of any one of Examples 1-4, wherein the non-moveable zone is depicted, via the user interface, as a plane or a line indicating a cutting plane.

Example 6: The method of any one of Examples 1-5, wherein the cutting planes define regions around the one or more 6 immoveable.

Example 7: The method of any one of Examples 1-6, wherein the non-moveable zone is geometrically aligned with the one or more implants.

Example 8: The system comprising at least one processor configured to perform the operations of: displaying, via a user interface, a model of a patient's teeth and the patient's palate and/or the buccal shelf area, wherein the palate and/or the buccal shelf area depict one or more implants; determining a non-moveable zone about the model; and generating multiple versions of an aligner configured to fit over the one or more implants and the patient's teeth, wherein the patient's teeth have movement with regard to successive versions of the aligner and as the non-moveable zone that remains in a fixed location.

Example 9: The system of Example 8, wherein the implants comprise any one of a temporary anchorage device or a palatal anchorage appliance.

Example 10: The system of any one of Examples 8-9, wherein the determining a non-moveable zone about the model comprises: receiving a user input for the selection of an area about the model designating a portion of the model non-moveable zone.

Example 11: The system of any one of Examples 8-10, wherein the non-moveable zone is depicted, via the user interface, as a border encompassing the one or more implants.

Example 12: The system of any one of Examples 8-11, wherein the non-moveable zone is depicted, via the user interface, as a plane or a line indicating a cutting plane.

Example 13: The system of any one of Examples 8-12, wherein the cutting planes define regions around the one or more implants that are immoveable.

Example 14: The system of any one of Examples 8-13, wherein the non-moveable zone is geometrically aligned with the one or more implants.

Example 15: Non-transitory computer storage medium that stores executable program instructions that when executed by at least one computing devices, configure the at least one computing devices to perform operations comprising: displaying, via a user interface, a model of a patient's teeth and the patient's palate and/or the buccal shelf area, wherein the palate and/or the buccal shelf area depict one or more implants; determining a non-moveable zone about the model; and generating multiple versions of an aligner configured to fit over the one or more implants and the patient's teeth, wherein the patient's teeth have movement with regard to successive versions of the aligner and as the non-moveable zone that remains in a fixed location.

Example 16: The non-transitory computer storage medium of Example 15, wherein the implants comprise any one of a temporary anchorage device or a palatal anchorage appliance.

Example 17: The non-transitory computer storage medium of any one of Examples 15-16, wherein the determining a non-moveable zone about the model comprises: receiving a user input for the selection of an area about the model designating a portion of the model non-moveable zone.

Example 18: The non-transitory computer storage medium of any one of Examples 15-17, wherein the non-moveable zone is depicted, via the user interface, as a border encompassing the one or more implants.

Example 19: The non-transitory computer storage medium of any one of Examples 15-18, wherein the non-moveable zone is depicted, via the user interface, as a plane or a line indicating a cutting plane.

Example 20: The non-transitory computer storage medium of any one of Examples 15-19, wherein the cutting planes define regions around the one or more implants that are immoveable.

Example 21: The non-transitory computer storage medium of any one of Examples 15-20, wherein the non-moveable zone is geometrically aligned with the one or more implants.

A number of embodiments have been described. Nevertheless, it will be understood that various modifications may be made without departing from the spirit and scope of the invention.

In addition, the logic flows depicted in the figures do not require the particular order shown, or sequential order, to achieve desirable results. In addition, other steps may be provided, or steps may be eliminated, from the described flows, and other components may be added to, or removed from, the described systems.

In the foregoing disclosure, implementations of the disclosure have been described with reference to specific example implementations thereof. It will be evident that various modifications may be made thereto without departing from the broader spirit and scope of implementations of the disclosure as set forth in the following claims. The disclosure and drawings are, accordingly, to be regarded in an illustrative sense rather than a restrictive sense.

What is claimed is:

1. A method of creating an orthodontic appliance:

displaying, via a user interface, a model of a patient's teeth and the patient's palate and/or the buccal shelf area, wherein the palate and/or the buccal shelf area depict one or more implants;

determining a non-moveable zone about the model; and generating multiple versions of an aligner configured to fit over the one or more implants and the patient's teeth, wherein the patient's teeth have movement with regard to successive versions of the aligner and as the non-moveable zone that remains in a fixed location, wherein the non-moveable zone is depicted, via the user interface, as a border encompassing the one or more implants.

2. The method of claim 1, wherein the implants comprise any one of a temporary anchorage device or a palatal anchorage appliance.

3. The method of claim 1, wherein the determining a non-moveable zone about the model comprises:

receiving a user input for the selection of an area about the model designating a portion of the model non-moveable zone.

4. The method of claim 1, wherein the non-moveable zone is depicted, via the user interface, as a plane or a line indicating a cutting plane.

5. The method of claim 4, wherein the cutting planes define regions around the one or more implants that are immoveable.

6. The method of claim 1, wherein the non-moveable zone is geometrically aligned with the one or more implants.

7. The system of claim 1, wherein the implants comprise any one of a temporary anchorage device or a palatal anchorage appliance.

8. The system of claim 1, wherein the determining a non-moveable zone about the model comprises:

receiving a user input for the selection of an area about the model designating a portion of the model non-moveable zone.

9. The system of claim 1, wherein the non-moveable zone is depicted, via the user interface, as a plane or a line indicating a cutting plane.

10. The system of claim 9, wherein the cutting planes define regions around the one or more implants that are immoveable.

11. The system of claim 1, wherein the non-moveable zone is geometrically aligned with the one or more implants.

12. A system comprising at least one processor configured to perform the operations of:

displaying, via a user interface, a model of a patient's teeth and the patient's palate and/or the buccal shelf area, wherein the palate and/or the buccal shelf area depict one or more implants;

determining a non-moveable zone about the model; and generating multiple versions of an aligner configured to fit over the one or more implants and the patient's teeth, wherein the patient's teeth have movement with regard to successive versions of the aligner and as the non-moveable zone that remains in a fixed location, wherein the non-moveable zone is depicted, via the user interface, as a border encompassing the one or more implants.

13. Non-transitory computer storage medium that stores executable program instructions that when executed by at least one computing devices, configure the at least one computing devices to perform operations comprising:

displaying, via a user interface, a model of a patient's teeth and the patient's palate and/or the buccal shelf area, wherein the palate and/or the buccal shelf area depict one or more implants;

determining a non-moveable zone about the model; and generating multiple versions of an aligner configured to fit over the one or more implants and the patient's teeth, wherein the patient's teeth have movement with regard to successive versions of the aligner and as the non-moveable zone that remains in a fixed location, wherein the non-moveable zone is depicted, via the user interface, as a border encompassing the one or more implants.

14. The non-transitory computer storage medium of claim 13, wherein the implants comprise any one of a temporary anchorage device or a palatal anchorage appliance.

15. The non-transitory computer storage medium of claim 13, wherein the determining a non-moveable zone about the model comprises:

receiving a user input for the selection of an area about the model designating a portion of the model non-moveable zone.

16. The non-transitory computer storage medium of claim 13, wherein the non-moveable zone is depicted, via the user interface, as a plane or a line indicating a cutting plane.

17. The non-transitory computer storage medium of claim 16, wherein the cutting planes define regions around the one or more implants that are immoveable.

18. The non-transitory computer storage medium of claim 13, wherein the non-moveable zone is geometrically aligned with the one or more implants.

* * * * *